(12) United States Patent
Jarecki-Black

(10) Patent No.: US 6,368,603 B1
(45) Date of Patent: Apr. 9, 2002

(54) LYME COMBINATION COMPOSITIONS AND USES

(75) Inventor: Judy Jarecki-Black, Carnesville, GA (US)

(73) Assignee: Merial Limited, Athens, GA (US)

( * ) Notice: Subject to any disclaimer, the term of this patent is extended or adjusted under 35 U.S.C. 154(b) by 0 days.

(21) Appl. No.: 08/812,348

(22) Filed: Mar. 5, 1997

(51) Int. Cl.$^7$ .................. A61K 39/02; A61K 49/00; A61K 39/38; A61K 39/12

(52) U.S. Cl. ............... 424/234.1; 424/9.1; 424/9.2; 424/184.1; 424/201.1; 424/202.1; 424/203.1; 424/204.1; 424/211.1; 424/215.1; 424/221.1; 424/828; 424/829

(58) Field of Search ............... 424/184.1, 234.1, 424/828, 829, 9.1, 9.2, 201.1, 202.1, 203.1, 204.1, 211.1, 213.1, 221.1

(56) References Cited

U.S. PATENT DOCUMENTS

| | | | |
|---|---|---|---|
| 5,266,313 A | | 11/1993 | Esposito et al. .............. 424/89 |
| 5,523,089 A | | 6/1996 | Bergstrom et al. ........ 424/262.1 |
| 5,554,371 A | | 9/1996 | Caputa et al. ............ 424/234.1 |
| 5,688,512 A | * | 11/1997 | Bergstrom et al. ....... 424/234.1 |
| 5,807,685 A | * | 9/1998 | Flavell et al. ................ 435/7.1 |
| 5,843,456 A | * | 12/1998 | Paoletti et al. ........... 424/199.1 |

FOREIGN PATENT DOCUMENTS

EP 465204 * 1/1992

OTHER PUBLICATIONS

Ma et al. Vaccine 14(14): 1366–74, 1996 (Oct.).*
Ma et al. J. of Infectious Diseases 171 (4) : 909–15, 1995 (Apr.).*
Coughlin et al. J. of Infectious Dis 171 (4) : 1049–52, 1995.*
Chang et al. Infection and Immunity 63(9) : 3543–9, 1995.*

* cited by examiner

*Primary Examiner*—Rodney P. Swartz
(74) *Attorney, Agent, or Firm*—Frommer Lawrence & Haug LLP; William S. Frommer; Thomas J. Kowalski

(57) ABSTRACT

Disclosed and claimed are compositions containing a *Borrelia burgdorferi* antigen, and methods for making and using them. The antigen can be OspA. The compositions can contain at least one additional antigen from a pathogen other than *Borrelia burgdorferi*. The compositions are useful for eliciting an immunological response in a host mammal susceptible to Lyme Disease and to the mammalian pathogen other than *Borrelia burgdorferi*. Suitable host mammals include dogs, pups, horses, and, the additional antigen can be of a canine, equine or feline pathogen, such as rabies, canine distemper, adenovirus, coronavirus, parainfluenza and parvovirus. No significant efficacy interference is observed.

23 Claims, 11 Drawing Sheets

FIG. 5.

PCR Oligos for Cloning into pCMB1 Expression Vector

B31

```
                                                                        BamHI
                                                    3'-GCGAAATTTATTCCTCCCTAGGGGC-5' CO3
5'-ATATATTATGAAAAATATTTATTGGGAATAGGTCT............AAAAACGCTTTAAAAATAAGGAG-3'
3'-TATATAATACTTTTTATAAATAACCCTTATCCAGA............TTTTGCGAAATTTATTCCTC-5'
5'-CGGCCATGGAAAAATATTTATTGGG-3' PK3
        NcoI
```

ACA1

```
                                                                        BamHI
                                                    3'-GCGAAACTTTATTTATTCCCTAGGGGC-5' BZ1
5'-ATATATTATGAAAAATATTTATTGGGAATAGGTCT......AACTTAAAAACGCTTGAAATAAATAAGGAG-3'
3'-TATATAATACTTTTTATAAATAACCCTTATCCAGA......TTGAATTTTTGCGAAACTTTATTTATTCCTC -5'
5'-CGGCCATGGAAAAATATTTATTGGG-3' PK3
        NcoI
```

IP90

```
                                                                        BamHI
                                                    3'-CTACGAAATTTATCCCTAGGGGC-5' PK4
5'-ATATATTATGAAAAATATTTATTGGGAATAGGTCT......AACTTAAAGATGCTTTAAAATAGGGAG-3'
3'-TATATAATACTTTTTATAAATAACCCTTATCCAGA...... ..TTGAATTTCTACGAAATTTATCCCTC-5'
5'-CGGCCATGGAAAAATATTTATTGGG-3' PK3
        NcoI
```

LYME COMBINATION COMPOSITIONS AND USES

RELATED APPLICATIONS

Reference is made to U.S. Pat. Nos. 5,582,990, 5,523,089 and applications Ser. Nos. PCT/US95/07665, PCT/US92/08972, WO93/08306, PCT/US95/07665, WO93/08299, PCT/US92/08697, PCT/US95/07709, WO95/35119 and WO90/04411, each of which is hereby incorporated herein by reference. Several documents are cited in this application, with full citation thereof where cited, or in the listing headed "References" before the claims; and, each document cited herein is hereby incorporated herein by reference.

FIELD OF THE INVENTION

The present invention relates to Lyme Disease (*Borrelia burgdorferi* antigen) compositions, especially combination compositions, and to methods of making and using the same, especially for veterinary uses. The compositions can include, in addition to a *Borrelia burgdorferi* antigen or antigens, an antigen for an additional pathogen, such as a canine, feline or equine pathogen, for instance an antigen from at least one of: rabies virus, canine distemper virus, adenovirus, corona virus, parainfluenza, parvovirus, FeLV, feline herpesvirus, equine influenza virus, equine herpes virus, and the like. The compositions advantageously induce an immunological response against Lyme Disease (*Borrelia burgdorferi*) infections, as well as against any other antigen in the composition, when administered to a host. The compositions elicit long-term immunity (response) against Lyme Disease *Borrelia burgdorferi* in animals, including horses and dogs, and afford protection or elicit immunological response in the animals. In combination compositions, there is an absence of efficacy interference.

The invention further relates to methods for making and using such compositions.

The invention additionally relates to the antibodies elicited by the compositions, isolated from an animal or cell culture as the case may be, which are useful for preparing a diagnostic kit, test or assay for the detection of a *Borrelia burgdorferi* antigen or Lyme Disease or another antigen of another pathogen or another pathogen.

BACKGROUND OF THE INVENTION

Lyme disease is a multisystem illness, transmitted by ticks of the *Ixodes ricinus* complex. The spirochaete *Borrelia burgdorferi* sensu lato is the aetiologic agent of Lyme disease, which is now the most common arthropod borne disease in the United States, and is endemic in Central Europe (Barbour et al., 1993). Although curable by antibiotic therapy in its early stages, if Lyme disease is allowed to progress, cardiac, neurological and joint abnormalities can arise. Investigations into the development of a human vaccine for Lyme disease are under way. The outer surface lipoprotein OspA of *Borrelia burgdorferi* is the current major candidate molecule for development of such a vaccine. Recombinant OspA lipoprotein (rOspA) is known to elicit a protective immune response in mice against challenge by infectious *B. burgdorferi* (Fikrig et al., 1990; Erdile et al., 1993; U.S. Ser. No. 08/373,455). OspA is currently undergoing human field trials as a subcutaneously administered vaccine in the United States (Keller et al., 1994).

Above-cited applications WO93/08299 and PCT/US92/08697 relate to recombinant OspA (rOspA) vaccines, especially lipidated rOspA, and methods for expressing DNA encoding OspA, and isolating the lipidated rOspA. Above-cited U.S. Pat. Nos. 5,582,990 and 5,523,089 and application WO 90/04411 relate to DNA encoding OspA, the amino acid sequence of OspA including rOspA and lipidated forms thereof, synthetic OspA including rOspA and lipidated forms thereof, compositions containing OspA or synthetic OspA, and methods of using such compositions. And, the other above-cited applications relate to DNA encoding other Borrelia antigens or other Osps, or to DNA encoding useful fragments of OspA or of other Osps, amino acid sequences thereof, compositions containing such fragments or other Osps, and methods for using such compositions. DNA from documents cited herein pertaining to *Borrelia burgdorferi* can be used in the methods of U.S. Pat. Nos. 5,582,990, and 5,523,089 or PCT/US92/08697 to produce OspA, other Borrelia antigens or Osps, or fragments thereof, for use in this invention. In regard to DNA and antigens useful in this invention, reference is also made to Molecular Microbiology (1989), 3(4), 479–486.

A particular problem in the art involves the infection of domesticated animals with *Borrelia burgdorferi* from tick bites. For instance, dogs and horses are susceptible to Lyme Disease due to tick bites, and their masters are unaware of the infection until it is too late (the tell-tale circular ring around the tick bite being undetected due to fur, and the dog or horse is unable to verbalize complaints such as sore joints, etc. from the infection, or due to masters not appreciating the subtle symptoms of the disease in animals). In addition, there is a concern about possible transmission to humans.

A further problem in the art involves vaccination strategies. More specifically, when vaccinating domesticated animals it is preferred to administer multiple antigens in one, "cocktail" or multivalent composition; for instance, to reduce the number of shots and number of visits to the veterinarian.

A Lyme Disease combination or "cocktail" or multivalent vaccine or immunological or immunogenic composition (*Borrelia burgdorferi* antigen in combination with other antigens in a composition, particularly for canines), is not presently available or known.

A still further problem in the art, especially as to multivalent composition, involves "efficacy interference", namely a failure of one or more antigens, in a combination composition to maintain or achieve efficacy. This is believed due to interference on that antigen stimulating an immunological, antigenic, antibody, or protective response in the host, e.g., dog, when administered, because of the presence of the other antigens. For instance, rabies antigens in a combination with other antigens suffer interference from or interfere with the stimulation of an immunological, antigenic, antibody or protective response by those other antigens in such a composition, especially when that composition is administered to dogs. More particularly, antigens, such as rabies antigens and Leptospira antigens, when administered with one or more other antigens can interfere with the response elicited by those antigens. Indeed, Leptospira antigens can interfere with OspA. However, for other hosts, such as cats, combination vaccines are known. Perhaps, without wishing to be bound by any one theory, the "efficacy interference" is due to some peculiarity of the canine biological system or, to the reaction with the canine biological system by presently known antigens or, by the combination thereof.

Regardless of the theory, there is heretofore to the inventor's knowledge, no known Lyme Disease combination with other antigenic composition, especially for canine use, and which does not exhibit efficacy interference. There is a need for a Lyme Disease combination, especially for canine use. It would indeed be surprising, unexpected and non-obvious to be able to formulate a Lyme Disease combination (with other antigens) composition which exhibits a lack of efficacy interference in canines, especially because as shown by the present knowledge and efficacy interference, one cannot simply combine "antigen compositions" to prepare a useful combination or "cocktail" composition.

Additionally, it would be advantageous if such a Lyme Disease antigen cocktail composition provided long term protection for canines, as well as protection for pups with maternal immunity to Lyme Disease. As the skilled artisan is aware, maternal immunity is immunity that a newborn acquires from its mother upon birth and/or from nursing, which immunity, after a period of time, lapses in the newborn, thereby leaving the newborn susceptible. Furthermore, the presence of maternal antibodies in the newborn prevents the newborn from obtaining a protective response when administered an antigen composition, e.g., a vaccine, thus meaning that the newborn must enter a period of no or little immunity, i.e., susceptibility, to the danger of the newborn before administration of an antigen or vaccine composition can be considered. In regard to maternal immunity, reference is made to U.S. Pat. No. 5,338,683, issued Aug. 16, 1994 and incorporated herein by reference.

Thus, alternative vaccination strategies are desirable.

It would even be more advantageous, surprising and unexpected if the *Borrelia burgdorferi* antigen which can be used in a combination "cocktail" composition which lacks efficacy interference in canines, can be used in such a composition for other hosts such as felines, equines and the like and, which provides long-term protection in dogs as well as protection in pups in spite of maternal immunity, was a recombinant antigen.

In particular, it is believed that heretofore the art has not taught or suggested administration to a mammalian host—especially a domesticated animal such as dogs, cats or horses—susceptible to Lyme disease, of a combination composition including a *Borrelia burgdorferi* antigen, e.g., OspA, especially as herein disclosed.

OBJECTS AND SUMMARY OF THE INVENTION

Immunization with a monovalent Lyme Disease (*Borrelia burgdorferi*) vaccine (designated Ly) is shown to be safe and efficacious in dogs, as assessed by both rate of seroconversion and protection against *Borrelia burgdorferi* infection.

Studies have now shown that a Lyme vaccine, containing 10 μg/ml OspA (prepared according to WO93/08299 and U.S. Pat. Nos. 5,582,990 and 5,523,089, incorporated herein by reference), provides dogs with significant protection against tick challenge, as assessed by both a reduction in spirochete proliferation and prevention of clinical disease. Furthermore this vaccine-induced immunity is still significant when challenge is five to six months after vaccination. The monovalent vaccine has also been shown to be exceptionally safe; dogs displaying clinical signs of Lyme Disease show no exacerbation of disease when vaccinated with repeated, high doses of the OspA vaccine.

However, it would be an even more significant advance in the art to provide a safe and efficacious combination Lyme vaccine. It would be a more significant advance to have lack of interference of the OspA vaccine when administered with other canine antigens. The herein results show that subcutaneous vaccinations, given at intervals, result in significant seroconversion. The level of antibody induced in these vaccinates is similar to that observed in dogs receiving the monovalent vaccine; levels which were shown to protect vaccinates including long term—against a challenge using Borrelia-infected ticks.

Because there is evidence that horses are also susceptible naturally to *Borrelia burgdorferi* infection, it would also be a significant advance to provide equine Lyme vaccines which result in the production of significant *Borrelia burgdorferi* antigen, e.g., OspA, antibody in horses.

It is an object of the present invention to provide a combination *Borrelia burgdorferi,* e.g., OspA, vaccine or immunological or antigenic composition, especially such a composition which induces protection in dogs, horses, or other domesticated animals.

It is another object of the present invention to provide a combination Lyme Disease vaccine or immunological or antigenic composition wherein there is no significant efficacy interference by the antigens in the combination.

It is a further object of the present invention to provide a Lyme Disease vaccine or immunological or antigenic composition for producing a serological response upon administration to dogs, horses or other domesticated animals.

Accordingly, the present invention provides an immunological antigenic or vaccine composition comprising an isolated purified *Borrelia burgdorferi* antigen, at least one additional antigen of a mammalian pathogen other than *Borrelia burgdorferi,* and optionally a pharmaceutically or veterinarily acceptable carrier.

In the composition, the isolated, purified *Borrelia burgdorferi* antigen can comprise isolated, purified OspA.

Further still, in the composition, the isolated, purified OspA can be an isolated, purified, lipidated recombinant OspA which is substantially free of lipopolysaccharide and substantially free of other bacterial proteins.

The composition can be without any immunogenicity enhancing adjuvant.

In the composition, the additional antigen can be selected from the group consisting of: an antigen of a canine pathogen, an antigen of an equine pathogen, and an antigen of a feline pathogen.

In certain preferred embodiments, in the composition, the additional antigen is an antigen of a canine pathogen or of an equine pathogen.

The additional antigen can be selected from the group consisting of: a rabies virus antigen, a canine distemper antigen, an adenovirus antigen, a coronavirus antigen, a parainfluenza antigen, a parvovirus antigen, and mixtures thereof.

In certain preferred embodiments of the composition, the additional antigen is a rabies virus antigen; or, the additional antigen comprises a canine distemper antigen, an adenovirus antigen, a coronavirus antigen, a parainfluenza antigen, and a parvovirus antigen.

The additional antigen can be a modified or attenuated live virus, e.g., an attenuated CDV, CAV such as CAV2, a coronavirus, a parainfluenza virus and/or a parvovirus.

The invention further comprehends a method for eliciting an immunological response in a mammal susceptible to Lyme Disease and to the mammalian pathogen other than *Borrelia burgdorferi* comprising administering to the mammal the aforementioned compositions.

The mammal can also be a horse and the additional antigen is of an equine pathogen. The mammal can also be a dog or pup and the additional antigen is of a canine pathogen.

Still further, the invention provides a method for eliciting an immunological response in a horse against *Borrelia burgdorferi* comprising administering to the horse a composition comprising isolated purified *Borrelia burgdorferi* OspA.

Even further, the invention provides a method for eliciting an immunological response in a dog or pup against *Borrelia burgdorferi* comprising administering to the dog or pup a composition comprising isolated, purified *Borrelia burgdorferi* OspA.

In these methods the OspA can be an isolated, purified lipidated recombinant OspA which is substantially free of lipopolysaccharide, and substantially free of other bacterial proteins. And, in these methods, the composition can be without any immunogenicity-enhancing adjuvant.

The invention also comprehends a method for preparing the aforementioned compositions comprising preparing the additional antigen in lyophilized form, preparing the *Borrelia burgdorferi* antigen in liquid form, and rehydrating the additional antigen with the *Borrelia burgdorferi* antigen.

The *Borrelia burgdorferi* OspA can be obtained by transforming a host organism by a plasmid containing a gene coding for a full-length wild-type *Borrelia burgdorferi* OspA lipoprotein and producing recombinant *Borrelia burgdorferi* OspA lipoprotein, and purifying said recombinant *Borrelia burgdorferi* OspA lipoprotein substantially free from other bacterial protein and from lipopolysaccharide under non-denaturing conditions from a lysate of said host organism.

For instance, useful in this invention is an isolated lipoprotein which comprises purified recombinant *Borrelia burgdorferi* OspA lipoprotein which has retained lipidation, is substantially free from other bacterial proteins and is substantially free from lipopolysaccharide, and the purified recombinant *Borrelia burgdorferi* OspA lipoprotein having been obtained by a process which comprises:

transforming a host organism by a plasmid containing a gene coding for a full-length wild-type *Borrelia burgdorferi* OspA lipoprotein and producing recombinant *Borrelia burgdorferi* OspA lipoprotein, purifying the recombinant *Borrelia burgdorferi* OspA lipoprotein substantially free from other bacterial protein and from lipopolysaccharide under non-denaturing conditions from a lysate of said host organism so as to obtain a purified recombinant *Borrelia burgdorferi* lipoprotein which remains lipidated and is immunogenic to a mammalian host when administered to the mammalian host.

The purifying of the recombinant *Borrelia burgdorferi* OspA can be by:

lysing cells of the host organism to obtain lysed cells;

treating the lysed cells with a surfactant which selectively solubilizes *Borrelia burgdorferi* OspA lipoprotein in preference to bacterial and other proteins and which is able to effect phase separation of a detergent phase under mild temperature conditions of about 35° to 40° C., to obtain treated lysed cells;

separating by phase separation the treated lysed cells into a detergent phase containing solubilized *Borrelia burgdorferi* OspA lipoprotein, an aqueous phase containing bacterial and other proteins and a solid phase containing cell residue;

separating the detergent phase from the solid and aqueous phases;

contacting the detergent phase with a chromatography column under conditions which result in binding of proteins other than *Borrelia burgdorferi* OspA lipoprotein to the chromatography column; and recovering flow-through from the first chromatography column containing the *Borrelia burgdorferi* OspA lipoprotein freed from the bound proteins.

The purifying of the recombinant *Borrelia burgdorferi* OspA can be by the contacting of the detergent phase with the chromatography column at a pH of about 7.5.

Alternatively, the OspA can be obtained by a process for the production of an isolated and purified recombinant OspA lipoprotein encoded by a full-length wild-type Borrelia opsa gene, which comprises:

effecting induction of Borrelia ospa lipoprotein from a host organism transformed by a plasmid containing the ospA gene, lysing the cells of the host organism, treating the lysed cells with a surfactant which selectively solubilizes Borrelia OspA lipoprotein in preference to bacterial and other proteins and which is able to effect phase separation of a detergent phase under mild conditions, effecting phase separation into a detergent phase containing solubilized Borrelia OspA lipoprotein, an aqueous phase containing bacterial and other proteins and a solid phase containing cell residue, separating the detergent phase from the solid phase and the aqueous phase, and purifying the detergent phase free from proteins other than Borrelia Ospa lipoprotein and lipopolysaccharide by:

(a) contacting the detergent phase with a first chromatography column under conditions which result in binding of proteins other than the Borrelia OspA lipoprotein to the first chromatography column, (b) recovering the flow through from the first chromatography column containing the Borrelia OspA lipoprotein freed from the bound proteins, (c) contacting the flow through from the first chromatography column with a second chromatography column under conditions to result in binding of the Borrelia OspA lipoprotein to the second chromatography column in preference to any residual contaminating proteins and lipopolysaccharide which flow through the second chromatography column, (d) contacting the second chromatography column with an eluant under conditions to elute the bound Borrelia OspA lipoprotein from the second chromatography column, and (e) collecting elute containing Borrelia OspA from said second chromatography.

Still further, in this process the contacting of the flow through with the second chromatography column can be effected at a pH of below about 5.7 and effective to bind the Borrelia OspA lipoprotein to the second chromatography column with an eluant is effected at a pH of up to and above about 5.7 and effective to elute bound Borrelia OspA lipoprotein from the second chromatography column.

And, even further still in this process the contacting of the detergent phase with the first chromatography column can be effected at a pH of approximately 7.5, the contacting of the flow through with the second chromatography column can be effected at a pH of approximately 4.2 and the contacting of the second chromatography column with an eluant can be effected at a pH of approximately 5.7.

The invention further comprehends antibodies elicited by the compositions and methods.

Surprisingly, no significant efficacy interference is observed from the inventive compositions and methods.

Other Borrelia antigens, for use in the compositions, methods and processes aforementioned in addition or in the alternative to OspA, are inter alia, as discussed in the applications and documents cited therein set forth under "Related Applications," including methods for preparing those other antigens.

Other objects and embodiments are disclosed in or are obvious from the following Detailed Description.

BRIEF DESCRIPTION OF THE DRAWINGS

In the following Detailed Description, reference is had to the following accompanying Figures, incorporated herein by reference, wherein:

FIG. 5 shows the PCR nucleotides used in cloning the B-31, ACA1 and Ip90 full-length ospA gene of *B. burgdorferi* into the pCMB1 expression vector;

DETAILED DESCRIPTION OF THE INVENTION

Figure 1:
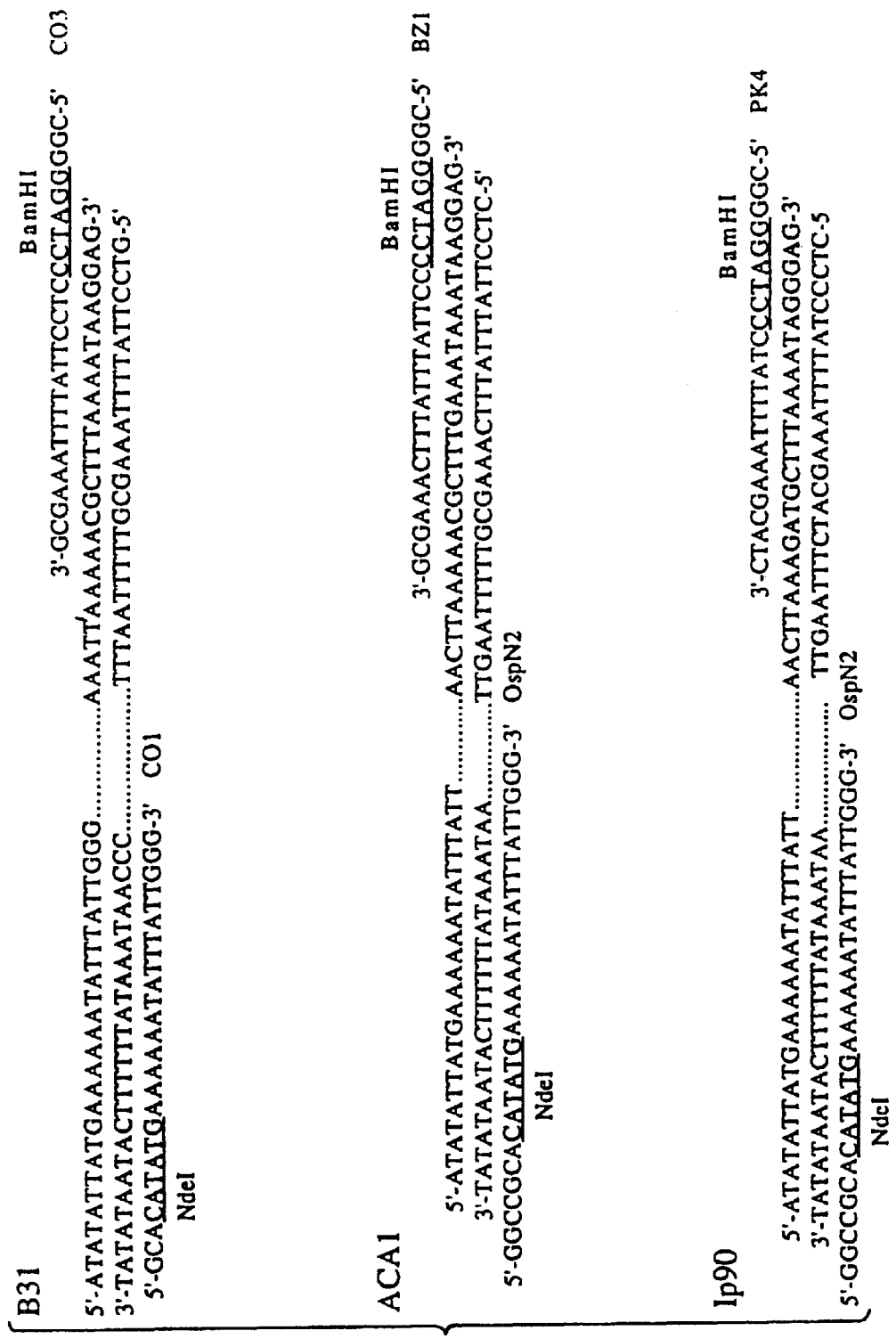
FIG. 1 shows the PCR oligonucleotides used in cloning the B-31, ACA1 and Ip90 full-length ospA gene of *B. burgdorferi* into the pET9a expression vector.

As discussed above, the invention provides *Borrelia burgdorferi* antigen-containing compositions, especially for use in domestic animals such as dogs, pups, cats, kittens and horses and the like. The composition are preferably "cocktail" or multivalent compositions. That is, the compositions preferably contain additional or "other" antigens of other pathogens.

The *Borrelia burgdorferi* antigen can be an epitope of interest of an antigen; and, the antigen is preferably OspA. The OspA is more preferably the expression product of a recombinant, such a *E. coli*. The ospA is preferably lipidated and thus, more preferably, the OspA is a recombinant OspA which is lipidated. The *Borrelia burgdorferi* antigen, e.g., OspA, can be obtained by any suitable method, such as by isolation from *Borrelia burgdorferi* cultures; or, preferably the recombinant lipidated OspA can be obtained by the methods disclosed in U.S. Pat. Nos. 5,582,990 and 5,523,089, and WO93/08299 incorporated herein by reference. In regard to *Borrelia burgdorferi* antigens and methods for preparing them, useful in the practice of this invention reference is also made to the documents cited under "Related Applications" and the documents cited therein.

The administration procedure for compositions of the invention such as immunological, antigenic or vaccine compositions or therapeutic compositions, including multivalent, "cocktail" or combination compositions, can be via a parenteral route (intradermal, intramuscular or subcutaneous). Such an administration enables a systemic immune response.

More generally, the inventive antigenic, immunological or vaccine *Borrelia burgdorferi* antigen compositions can be prepared in accordance with standard techniques well known to those skilled in the pharmaceutical or veterinary art. Such compositions can be administered in dosages and by techniques well known to those skilled in the medical or veterinary arts taking into consideration such factors as the age, sex, weight, species and condition of the particular patient, and the route of administration. The *Borrelia burgdorferi* antigen can be administered alone, or can be co-administered or sequentially administered with "other" antigen(s) or "other" immunological, antigenic or vaccine compositions thereby providing "cocktail" or combination compositions or administrations of the invention, and methods employing them. The "other" antigen(s) or "other" immunological, antigenic or vaccine compositions can be an epitope or epitopes of interest of such antigen(s), or compositions containing an epitope or epitopes of interest of such antigen(s).

Such "other" compositions can include isolated and/or purified antigens from any animal pathogen such as an antigen of a domesticated animal pathogen, for instance, any antigen of a canine, feline, equine or the like pathogen, e.g., one of: an antigen or antigens of a canine pathogen such as rabies, e.g., rabies glycoprotein G, canine distemper virus antigen, e.g., CDV HA and/or F glycoproteins, canine adenovirus type 2 antigen, canine coronavirus antigen, canine parainfluenza antigen, canine parvovirus antigen, Leptospira Canicola-Icterohaemorrhagiae Bacterin antigen, any combination of these antigens; or an antigen or antigens of a feline pathogen such as feline leukemia virus antigens, feline immunodeficiency virus antigens, rabies, feline herpesvirus antigen, or any combination of these antigens; or an antigen of an equine pathogen, e.g., an equine influenza and/or an equine herpes virus and/or rabies antigen. These "other" antigens can be from expression of such antigens by a recombinant, e.g., poxvirus or other vector system in vitro; or, such "other" compositions can include a recombinant, e.g., a poxvirus or poxviruses which express(es) the antigen (s) in vivo.

The methods for making a vector or recombinant for expression of OspA or an epitope of interest thereof, or of an "other" antigen or an epitope of interest thereof for use in this invention, can be by or analogous to the methods disclosed in U.S. Pat. Nos. 4,603,112, 4,769,330, 5,174,993, 5,505,941, 5,338,683, 5,494,807, 4,722,848, Paoletti, "Applications of pox virus vectors to vaccination: An update," PNAS USA 93:11349–11353, October 1996, Moss, "Genetically engineered poxviruses for recombinant gene expression, vaccination, and safety," PNAS USA 93:11341–11348, October 1996, Smith et al., U.S. Pat. No. 4,745,051 (recombinant baculovirus), Richardson, C. D.

(Editor), *Methods in Molecular Biology* 39, "Baculovirus Expression Protocols" (1995 Humana Press Inc.), Smith et al., "Production of Huma Beta Interferon in Insect Cells Infected with a Baculovirus Expression Vector," Molecular and Cellular Biology, December, 1983, Vol. 3, No. 12, p. 2156–2165; Pennock et al., "Strong and Regulated Expression of *Escherichia coli* B-Galactosidase in Infect Cells with a Baculovirus vector," Molecular and Cellular Biology Mar. 1984, Vol. 4, No. 3, p. 399–406; EPA 0 370 573, U.S. application Ser. No. 920,197, filed Oct. 16, 1986, EP Patent publication No. 265785, U.S. Pat. No. 4,769,331 (recombinant herpesvirus), Roizman, "The function of herpes simplex virus genes: A primer for genetic engineering of novel vectors," PNAS USA 93:11307–11312, October 1996, Andreansky et al., "The application of genetically engineered herpes simplex viruses to the treatment of experimental brain tumors," PNAS USA 93:11313–11318, October 1996, Robertson et al. "Epstein-Barr virus vectors for gene delivery to B lymphocytes," PNAS USA 93:11334–11340, October 1996, Frolov et al., "Alphavirus-based expression vectors: Strategies and applications," PNAS USA 93:11371–11377, October 1996, Kitson et al., J. Virol. 65, 3068–3075, 1991; U.S. Pat. Nos. 5,591,439, 5,552,143, Grunhaus et al., 1992, "Adenovirus as cloning vectors," Seminars in Virology (Vol. 3) p. 237–52, 1993, Ballay et al. EMBO Journal, vol. 4, p. 3861–65, Graham, Tibtech 8, 85–87, April, 1990, Prevec et al., J. Gen Virol. 70, 429–434, PCT WO91/11525, Felgner et al. (1994), J. Biol. Chem. 269, 2550–2561, Science, 259:1745–49, 1993 and McClements et al., "Immunization with DNA vaccines encoding glycoprotein D or glycoprotein B, alone or in combination, induces protective immunity in animal models of herpes simplex virus-2 disease," PNAS USA 93:11414–11420, October 1996, and U.S. Pat. Nos. 5,591, 639, 5,589,466, and 5,580,859 relating to DNA expression vectors, inter alia.

Again, the ingredients and manner (sequential or co-administration) of administration, as well as dosages can be determined taking into consideration such factors as the age, sex, weight, species and condition of the particular patient, and, the route of administration. In this regard, mention is also made of U.S. Pat. Nos. 5,503,834, 5,529, 780, 5,482,713 and 5,494,807 which include a disclosure of antigens of canine, feline and equine pathogens, recombinants expressing those antigens, and compositions containing those recombinants, as well as of copending: application Ser. No. 08/413,118 filed Mar. 29, 1995, directed to nucleotide and amino acid sequences of canine herpesvirus antigens and recombinants therefrom and uses thereof; applications Ser. Nos. 08/224,657, filed Apr. 6, 1994 and Ser. No. 08/416,616 filed Apr. 5, 1995, directed to poxvirus-canine distemper virus (CDV) recombinants and compositions and methods employing those recombinants; application Ser. No. 08/675,556, filed Jul. 3, 1996 directed to expression cassettes, promoters and recombinants, including canine adenovirus recombinants for veterinary applications; application Ser. No. 08/746,668, filed Nov. 14, 1996 which includes recombinants expressing feline immunodeficiency virus epitopes of interest; and, application Ser. No. 08/486, 969, filed Jun. 7, 1995 directed to recombinant poxvirus—rabies compositions, including combination compositions and uses thereof. Each of these patents and applications is hereby incorporated herein by reference, especially insofar as recombinants, expression products therefrom and nucleic acid coding disclosed in these applications can be employed in "cocktail", multivalent or combination compositions or administrations or recombinants thereof of the present invention.

For instance, Canine Distemper-Adenovirus Type 2-Coronavirus-Parainfluenza-Parvovirus$_{XL}$, Modified Live Virus (Product Code 1491.21) is a product. It would be highly advantageous to include a *Borrelia burgdorferi* antigen, e.g., OspA, with this product in a single unit package, i.e., as a combination composition; or to administer to a suitable host mammal, e.g., a canine, within the course of a single visit to a veterinarium, both the OACPiP$_{XL}$ and the *Borrelia burgdorferi* antigen.

Examples of compositions of the invention include liquid preparations for orifice, e.g., oral, nasal, anal, vaginal, peroral, intragastric, etc., administration such as suspensions, syrups or elixirs; and, preparations for parenteral, subcutaneous, intradermal, intramuscular or intravenous administration (e.g., injectable administration) such as sterile suspensions or emulsions. In such compositions the antigen(s) may be in admixture with a suitable carrier, diluent, or excipient such as sterile water, physiological saline, glucose or the like. The compositions can also be lyophilized. The compositions can contain auxiliary substances such as wetting or emulsifying agents, pH buffering agents, adjuvants, gelling or viscosity enhancing additives, preservatives, flavoring agents, colors, and the like, depending upon the route of administration and the preparation desired. Standard texts, such as "REMINGTON'S PHARMACEUTICAL SCIENCE", 17th edition, 1985, incorporated herein by reference, may be consulted to prepare suitable preparations, without undue experimentation. Suitable dosages can also be based upon the examples below. Typical canine dosages of *Borrelia burgdorferi* antigen can be 5 to 25 µg/ml, e.g., 13 µg/ml OspA, and typical equine dosages of *Borrelia burgdorferi* antigen can be 15 to 150 µg/dose, e.g., 100 µg/dose OspA alone, 30 µg/dose OspA alone, or 30 µg/dose OspA in combination with another antigen such as rabies (Imrab is a commercially available rabies vaccine with which the *Borrelia burgdorferi* antigen can be combined).

As mentioned above, antigenic, immunological or vaccine compositions typically can contain an adjuvant and an amount of the antigen(s) to elicit the desired response. In certain applications, alum (aluminum phosphate or aluminum hydroxide) is a typical adjuvant. Saponin and its purified component Quil A, Freund's complete adjuvant and other adjuvants are used in veterinary applications.

However, lipidated recombinant OspA can elicit a protective response without any necessity of adding an adjuvant.

Chemically defined preparations such as muramyl dipeptide, monophosphoryl lipid A, phospholipid conjugates such as those described by Goodman-Snitkoff et al. *J. Immunol.* 147:410–415 (1991) and incorporated by reference herein, encapsulation of the protein within a proteoliposome as described by Miller et al., *J. Exp. Med.* 176:1739–1744 (1992) and incorporated by reference herein, and encapsulation of the protein in lipid vesicles such as Novasome™ lipid vesicles (Micro Vescular Systems, Inc., Nashua, N.H.) can also be used.

The inventive composition may be packaged in a single dosage form for immunization by parenteral (i.e., intramuscular, intradermal or subcutaneous) administration or orifice administration, e.g., perlingual (i.e., oral), intragastric, mucosal including intraoral, intraanal, intravaginal, and the like administration. And again, the effective dosage and route of administration are determined by the nature of the composition, and by known factors, such as breed or species, age, sex, weight, condition and nature of host, as well as $LD_{50}$ and other screening procedures which are known and do not require undue experimentation. Dosages can generally range from a few to a few hundred micrograms, e.g., 5 to 500 µg of each antigen. Other suitable carriers or diluents can be water or a buffered saline, with or without a preservative. The antigen(s) may be lyophilized for resuspension at the time of administration or can be in solution.

The carrier may also be a polymeric delayed release system. Synthetic polymers are particularly useful in the formulation of a composition having controlled release. An early example of this was the polymerization of methyl methacrylate into spheres having diameters less than one micron to form so-called nano particles, reported by Kreuter, J., *Microcansules and Nanoparticles in Medicine and Pharmacoloqy,* M. Donbrow (Ed). CRC Press, p. 125–148.

Microencapsulation has been applied to the injection of microencapsulated pharmaceuticals to give a controlled release. A number of factors contribute to the selection of a particular polymer for microencapsulation. The reproducibility of polymer synthesis and the microencapsulation process, the cost of the microencapsulation materials and process, the toxicological profile, the requirements for variable release kinetics and the physicochemical compatibility of the polymer and the antigens are all factors that must be considered. Example of useful polymers are polycarbonates, polyesters, polyurethanes, polyorthoesters and polyamides, particularly those that are biodegradable.

A frequent choice of a carrier for pharmaceuticals and more recently for antigens is poly (d,1-lactide-co-glycolide) (PLGA). This is a biodegradable polyester that has a long history of medical use in erodible sutures, bone plates and other temporary prostheses where it has not exhibited any toxicity. A wide variety of pharmaceuticals including peptides and antigens have been formulated into PLGA microcapsules. A body of data has accumulated on the adaption of PLGA for the controlled release of antigen, for example, as reviewed by Eldridge, J. H., et al. *Current Topics in Microbiology and Immunology.* 1989, 146:59–66. The entrapment of antigens in PLGA microspheres of 1 to 10 microns in diameter has been shown to have a remarkable adjuvant effect when administered orally. The PLGA microencapsulation process uses a phase separation of a water-in-oil emulsion. The compound of interest is prepared as an aqueous solution and the PLGA is dissolved in a suitable organic solvents such as methylene chloride and ethyl acetate. These two immiscible solutions are co-emulsified by high-speed stirring. A non-solvent for the polymer is then added, causing precipitation of the polymer around the aqueous droplets to form embryonic microcapsules. The microcapsules are collected, and stabilized with one of an assortment of agents (polyvinyl alcohol (PVA), gelatin, alginates, polyvinylpyrrolidone (PVP), methyl cellulose) and the solvent removed by either drying in vacuo or solvent extraction.

Microencapsulation, delay release system, and encapsulation techniques, for instance, as above discussed, can have a use when delaying presentation of one or more antigens in a combination composition to the immune system is desired.

Thus, liquid, including by injection or other administration, as well as solid, including solid-containing-liquid, liquid, and gel (including "gel caps") compositions are envisioned.

Further, the inventive compositions can be used directly to stimulate an immune response in animals. That immune response can be an antibody response; and therefore, from those antibodies, by techniques well-known in the art, monoclonal antibodies can be prepared and, those monoclonal antibodies can be employed in well known antibody binding assays, diagnostic kits or tests to determine the presence or absence of particular antigen(s). Those monoclonal antibodies can also be employed in immunoadsorption chromatography to recover or isolate antigen(s).

Methods for producing monoclonal antibodies and for uses of monoclonal antibodies are well known to those of ordinary skill in the art. They can be used in diagnostic methods, kits, tests or assays, as well as to recover materials by immunoadsorption chromatography or by immunoprecipitation.

Monoclonal antibodies are immunoglobulins produced by hybridoma cells. A monoclonal antibody reacts with a single antigenic determinant and provides greater specificity than a conventional, serum-derived antibody. Furthermore, screening a large number of monoclonal antibodies makes it possible to select an individual antibody with desired specificity, avidity and isotype. Hybridoma cell lines provide a constant, inexpensive source of chemically identical antibodies and preparations of such antibodies can be easily standardized. Methods for producing monoclonal antibodies are well known to those of ordinary skill in the art, e.g., Koprowski, H. et al., U.S. Pat. No. 4,196,265, issued Apr. 1, 1989, incorporated herein by reference.

Uses of monoclonal antibodies are known. One such use is in diagnostic methods, e.g., David, G. and Greene, H. U.S. Pat. No. 4,376,110, issued Mar. 8, 1983; incorporated herein by reference. Monoclonal antibodies have also been used to recover materials by immunoadsorption chromatography, e.g., Milstein, C. 1980, Scientific American 243:66, 70, incorporated herein by reference.

Accordingly, the inventive compositions have several hereinstated utilities. Other utilities also exist for embodiments of the invention.

A better understanding of the present invention and of its many advantages will be had from the following examples, given by way of illustration.

EXAMPLES

Example 1

Preparation of Recombinant OspA

Recombinant OspA was produced as described in U.S. Pat. Nos. 5,523,089, and 5,582,990, WO93/08299, PCT/US92/08697 and Erdile et al. 1993. In short:

The cloned ospA gene of *B. burgdorferi* strain B31 (as described in the above-mentioned WO 90/04411) (N-terminal region: SEQ ID NO: 1, c-terminal region: SEQ ID NO: 2. The remainder of the sequence is shown in WO 90/04411) was used as a template (pTRH44; Howe et al., 1986, Infection and Immunity, 54:207–212, "Howe et al. 1986") and specially-designed oligonucleotide primers (PET-IN [CO1] (SEQ ID NO: 3) and PET-273C [CO3] (SEQ ID NO: 4)) were used in a polymerase chain reaction (PCR) to amplify the whole of the wild-type ospA gene, as shown in FIG. 1.

Similarly, the cloned ospA gene of *B. burgdorferi* strains ACA1 and Ip90 (as described in Johnsson et al., 1992, Infect. Immun. 60:1845–1853 - N-terminal region of ACA1 and Ip90 is: SEQ ID NO: 1; C-terminal region of ACA1: SEQ ID NO: 5; C-terminal region of Ip90: SEQ ID NO: 6) was used in a PCR reaction with oligonucleotide primer pairs (a) OspN2 (SEQ ID NO: 7) and BZ1 (SEQ ID NO: 8)

and (b) OspN 2 (SEQ ID NO: 7) and pK4 (SEQ ID NO: 9), respectively at the N- and C-terminal ends to form the appropriate amplified fragments, as shown in FIG. 1.

The basic methods for amplifying a desired target nucleic acid sequence using oligonucleotide primers are generally known in the art and are described in U.S. Pat. Nos. 4,683,202 and 4,800,159. Reference may be had to such patents for description of the techniques to be employed.

Figure 2:
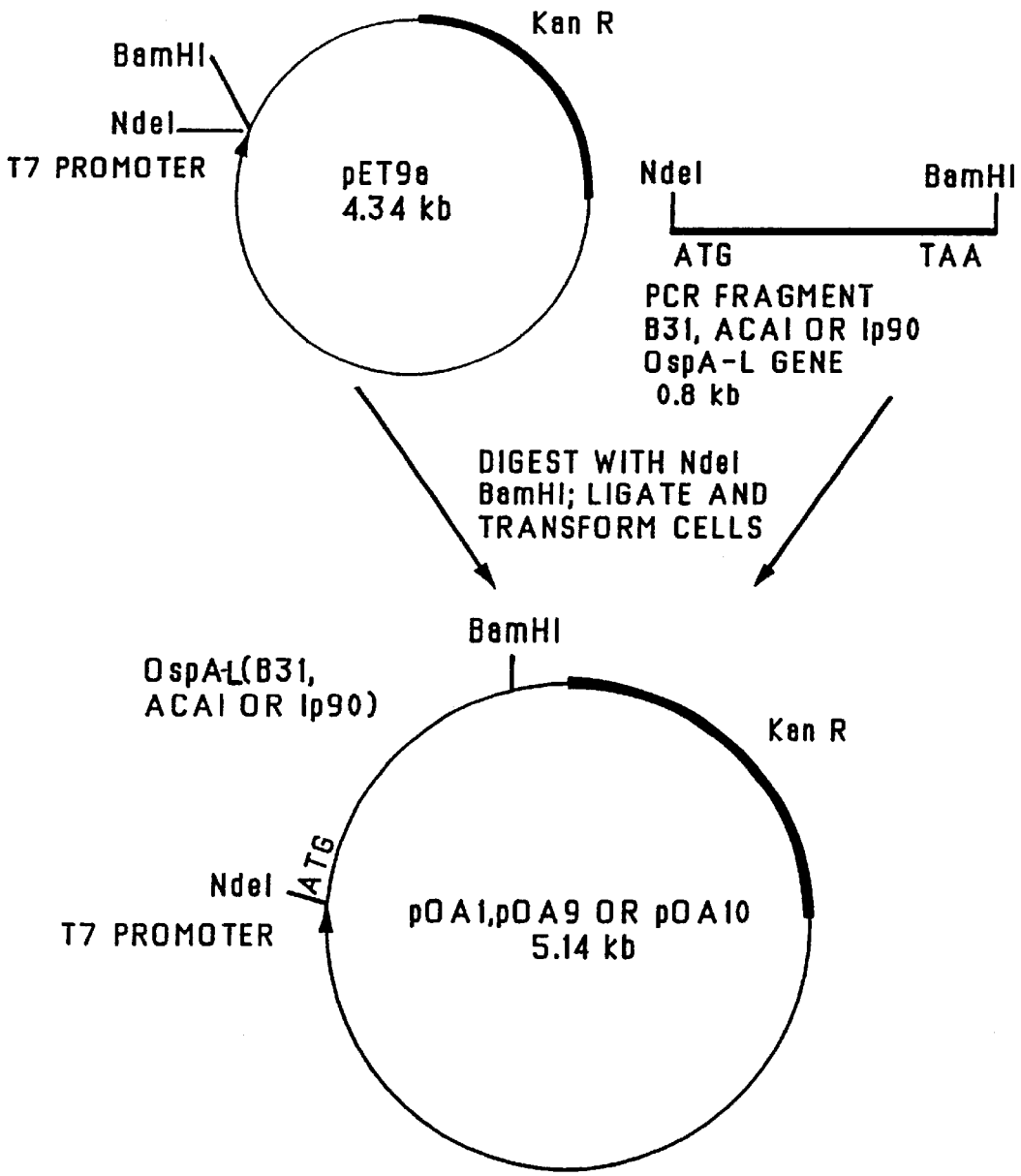
FIG. 2 illustrates the cloning strategy for inserting the full-length ospA gene into the pET9a expression vector so as to place the ospA gene under control of the T7 Ø 10 promoter, to form pOA1 from the B31 gene, pOA9 from the ACA1 gene and pOA10 from the Ip90 gene.

The resulting fragments were cloned into the NdeI and Bam HI sites of the plasmid vector pET9 to place the ospA gene under control of a T7 promoter and efficient translation initiation signals from bacteriophage T7, as seen in FIG. 2. The pET9 and pLysS plasmids, the bacterial hosts for cloning, growth media and the methods used to direct expression of cloned genes by T7 RNA polymerase have previously been described in U.S. Pat. No. 4,952,496 and reference may be had thereto for such description. While a T7 promoter system is one preferred expression system in the present invention, expression of the full-length ospA gene may be achieved utilizing other expression systems compatible with the host organism.

The pET9 expression vector was used since it has a kan gene as its selective marker rather than a bla gene. Consequently, ampicillin is not used during cell growth and hence there is no possibility that an immunogenic ampicilloyl/OspA target protein conjugate can be formed. Such conjugates are believed to be major antigenic determinants in penicillin allergy and may complicate immunological studies.

Figure 3:
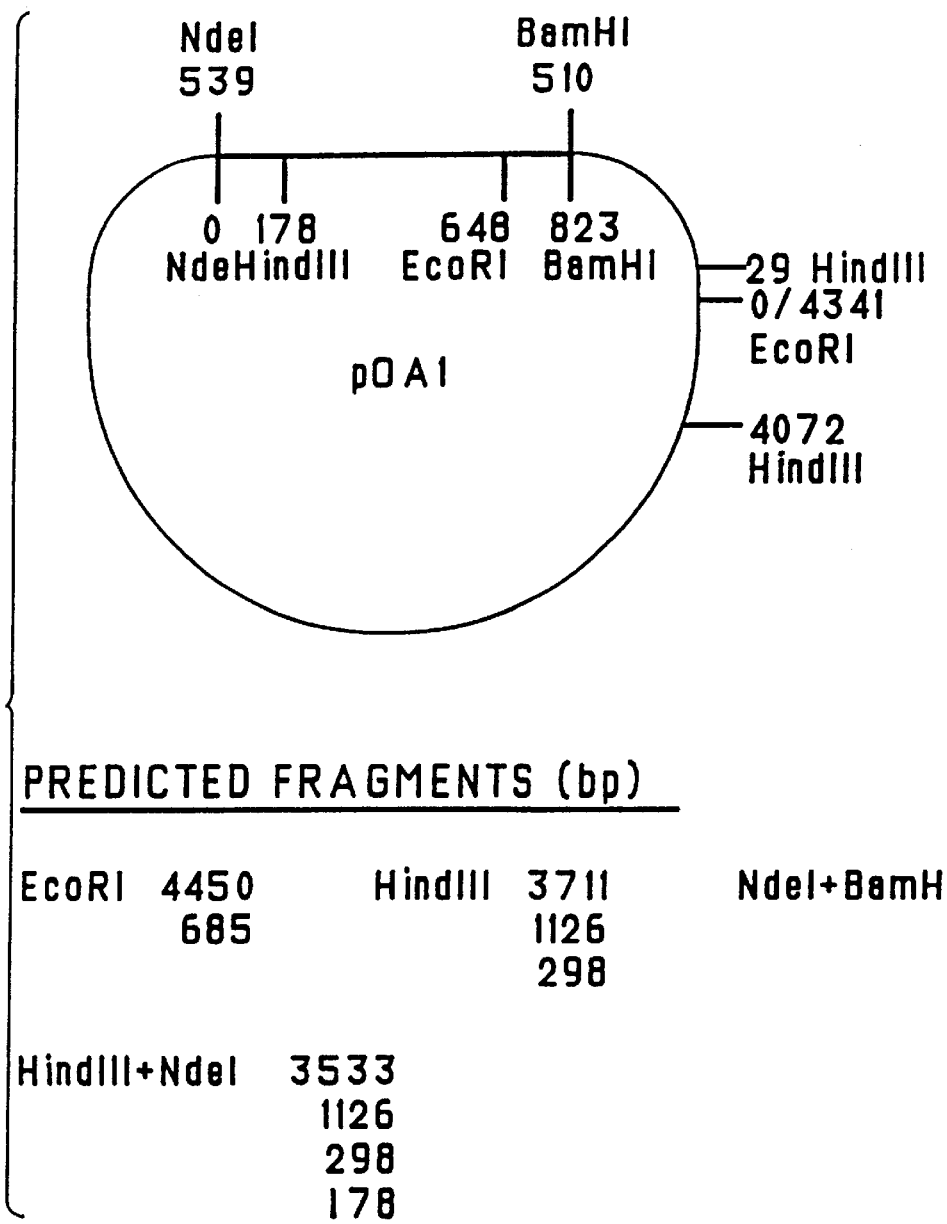
FIG. 3 is a predicted restriction map of plasmid pOA1.
Figure 4:
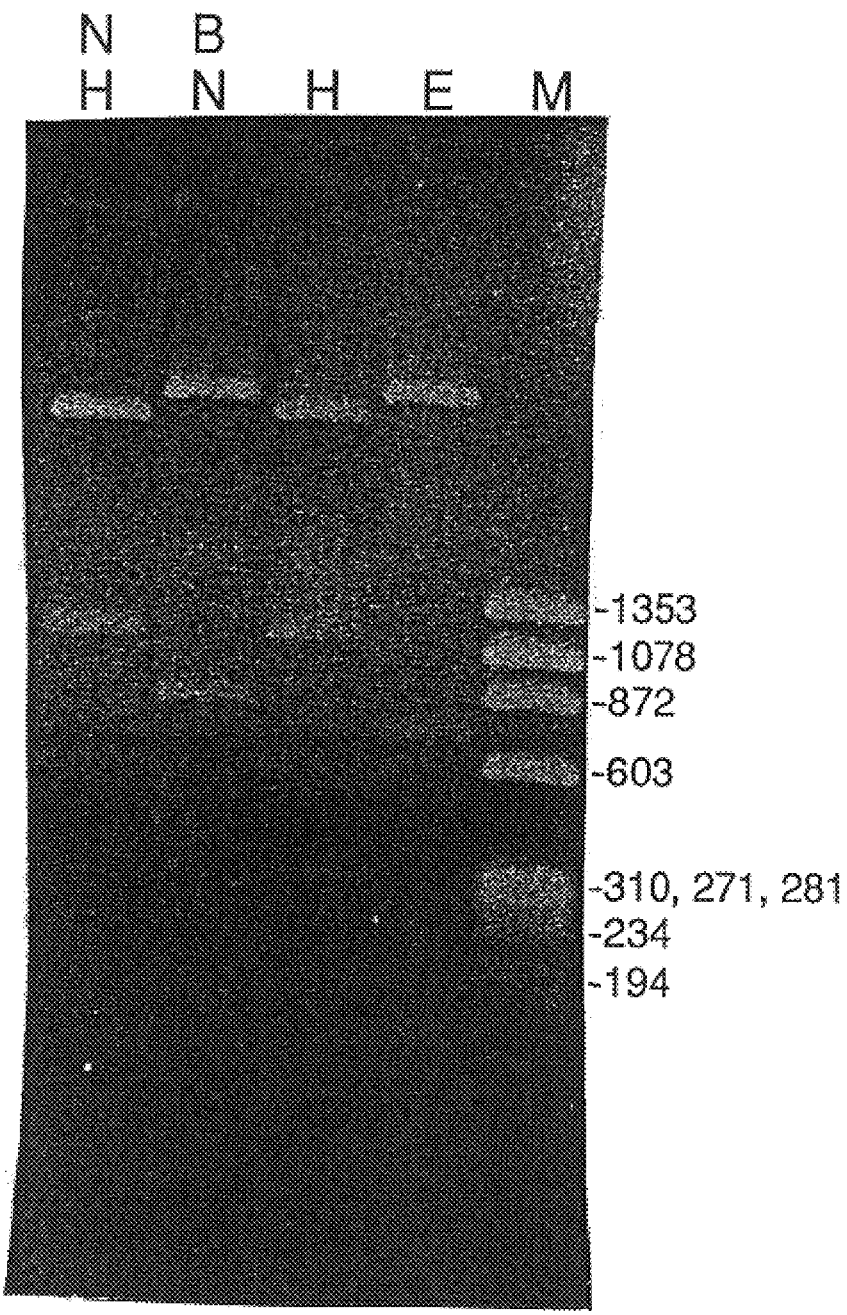
FIG. 4 shows the results of various restriction digests of plasmid pOA1, demonstrating that all predicted sites are present (M=markers (ØX 174 DNA digested with Hae III); B=Bam HI; E=Eco RI; H=Hind III; N=Nde I)

The resulting plasmids have been designated pOA1, pOA9 and pOA10, containing the ospA genes from B31, ACA1 and Ip90 strains of *B. burgdorferi*, respectively. The pOA1 plasmid is nearly identical to the pET9-preospA plasmid described by Dunn et al., 1990, Protein Expression and Purification, 1:159–168, except that the oligonucleotides used for the PCR reaction were different in the two cases. A predicted restriction map for the plasmid pOA1 is shown in FIG. 3, while FIG. 4 contains the results of various restriction digests of plasmid pOA1, demonstrating that all the predicted sites are present.

Figure 7A:
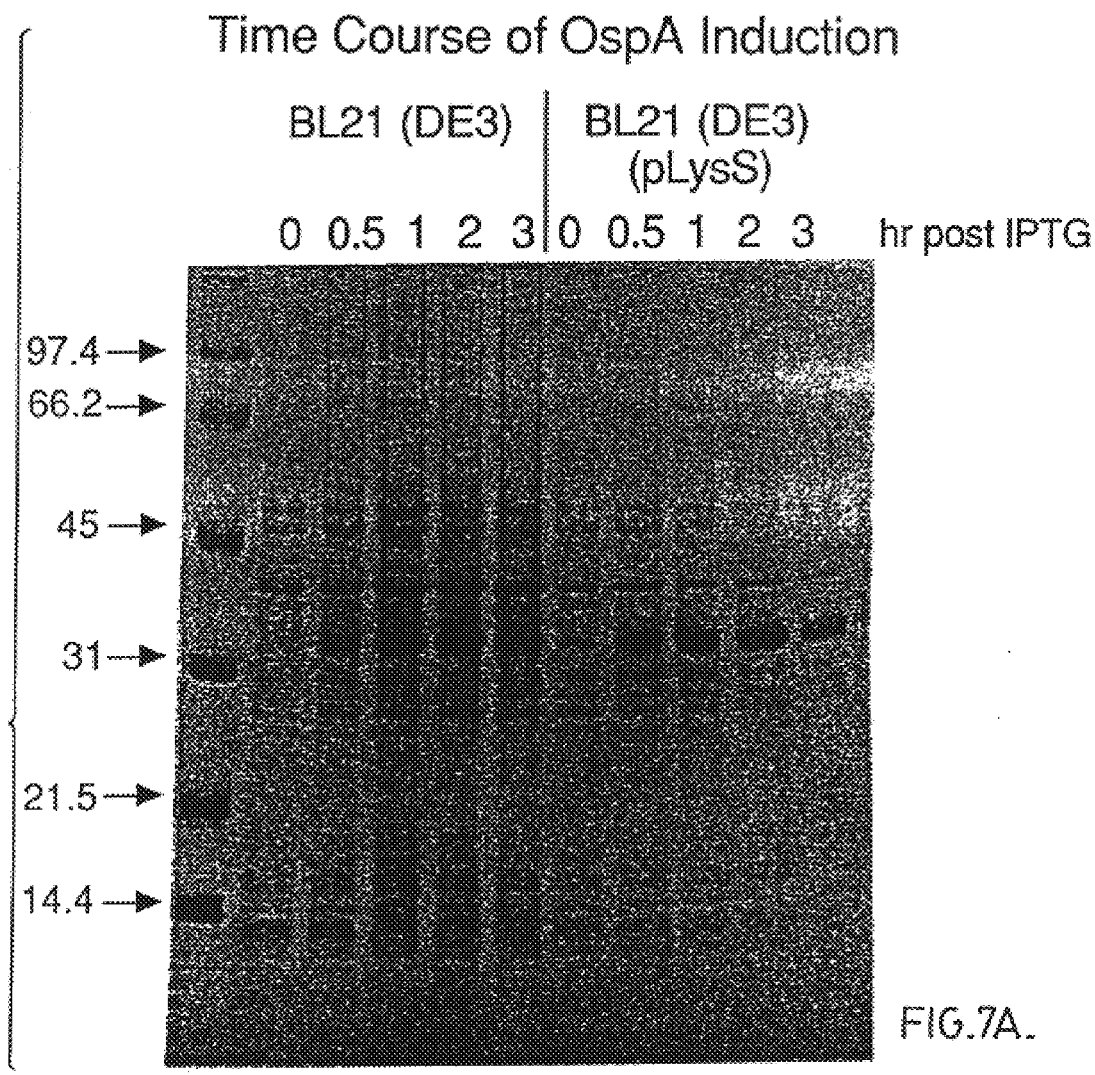
FIGS. 7A, 7B and 7C show a time course of induction with ITPG of Ospa in two host strains containing pOA1 (FIG. 7A), and a host strain containing pOA5 (FIG. 7B) and pOA6 (FIG. 7C)

For protein production, the plasmids pOA1, pOA9 and pOA10 were transformed into the expression strain of *E. coli*, preferably, the *E. coli* strain is the T7 expression strain of *E. coli*, as described in the aforementioned U.S. Pat. No. 4,952,496. Specifically, the strain may be the expression strain BL21(DE3)(pLysS) of *E. coli*, as described above, or *E. coli* strain HMS174(DE3)(pLysS). The transformed host was grown and protein was induced with isopropyl-β-D-thiogalactoside (IPTG). A time course of induction of OspA from plasmid pOA1, following IPTG addition, is shown in FIG. 7A. Identical results to those for pOA1 were obtained using pOA9 and pOA10. Synthesis of OspA protein from plasmid pOA1 ceased approximately one hour after induction, implying some toxicity of the protein to *E. coli*. Nevertheless, the protein production was at an acceptable level of approximately 10 mg/L of cell culture.

Figure 6:
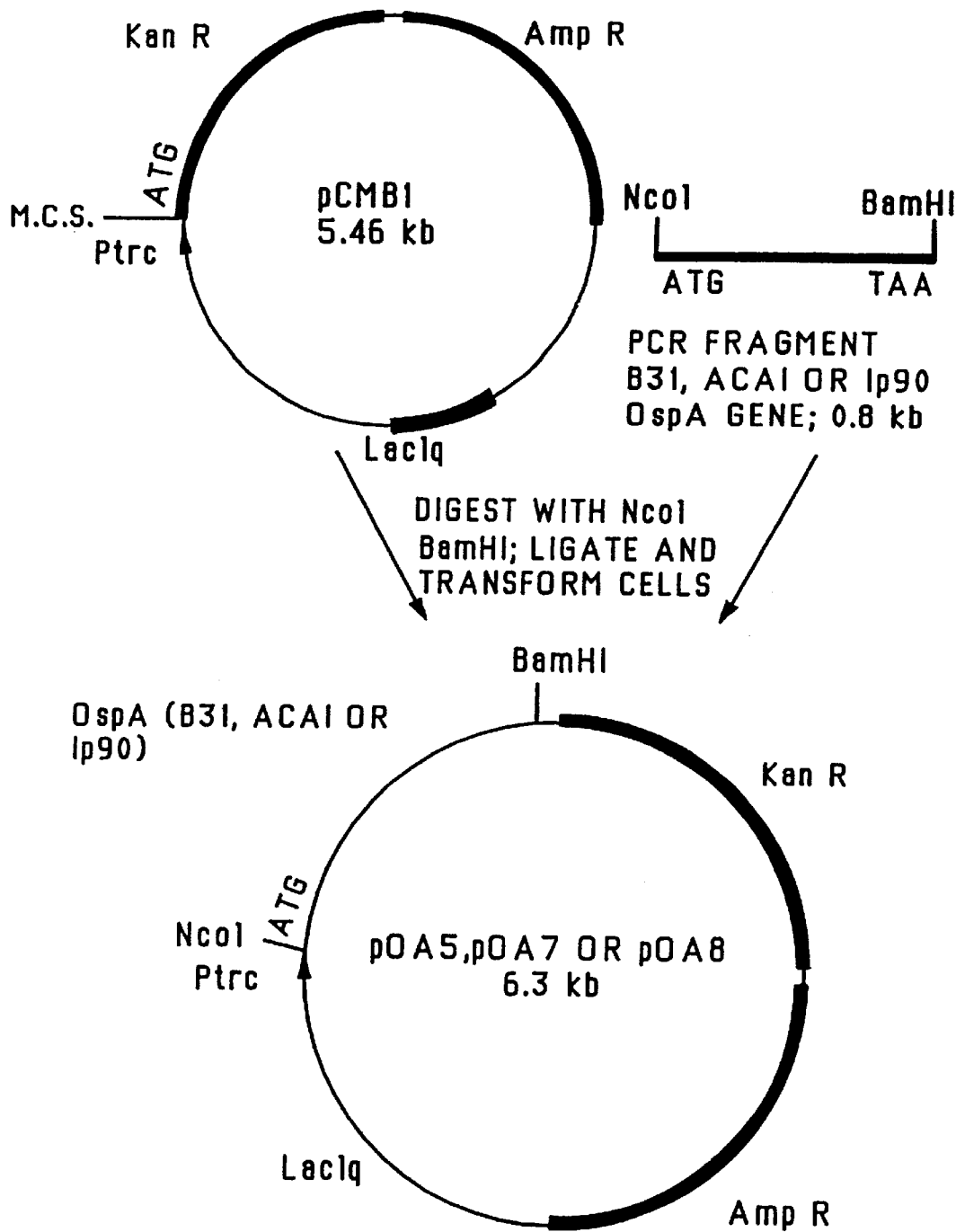
FIG. 6 illustrates the cloning strategy for inserting the full-length ospA gene into the pCMB1 expression vector, so as to place the ospA gene under the control of the Trc promoter, to form pOA5 from the B31 gene, pOA7 from the ACA1 gene and pOA8 from the Ip90 gene.

In addition to the provision of plasmids pOA1, pOA9 and pOA10 and expression of OspA lipoprotein in *E. coli* using the T7 promoter, further plasmids have been constructed containing the full-length B31, ACA1 and Ip90 ospA gene under a different promoter and expression of lipoprotein has been achieved. In this regard, plasmids pOA5 and pOA6 were prepared by cloning the PCR-amplified fragment of ospA from B31 stain into the Nco1 and Bam HI sites of plasmid expression vectors pCMB1 and pCMB2 while plasmids pOA7 and pOA8 were prepared by cloning a PCR-amplified fragment of OspA from ACA1 strain (pOA7) and from Ip90 strain (pOA8) into the Nco1 and Bam HI sites of expression vector pCMB1 (see FIG. 6 for pOA5, pOA7 and pOA8).

As seen in FIG. 5, the cloned ospA genes of *B. burgdorferi* strains B31, ACA1 and Ip90 were amplified by PCR reaction using oligonucleotide primer pairs (a) PK3 (SEQ ID NO:10) and CO3 (SEQ ID NO:3), (b) PK3 and (SEQ ID NO: 10) and BZ1 (SEQ ID NO: 8), and (c) PK3 (SEQ ID NO: 10) and PK4 (SEQ ID NO: 9), respectively at the N- and C-terminal ends of the respective genes to form the appropriate amplified fragments.

Plasmids pCMB1 and pCMB2 were constructed by digesting plasmid pTrc99a (Pharmacia Catalog No. 27-5007-01) and a Kanamycin resistance gene (Pharmacia Catalog No. 27-4897-01), isolating the resulting fragments together (FIG. 9). Plasmid pTrc99a, 4197 bp, contains a strong promoter adjacent to a multiple cloning site, followed by a strong transcription termination signal (rrnB). Expression of the target gene uses the host cell RNA polymerase, allowing its use in a wide variety of *E. coli* strains. Expression is tightly controlled by the lactose suppressor gene (lacIq) included on the vector. The lactose repressor protein prevents transcription of the target gene in the absence of the inducer IPTG. The kanamycin resistance gene is a linear double stranded 1282 bp DNA fragment containing the gene from the transposon Tn903 flanked by restriction enzyme sites and encodes the enzyme aminoglycoside 3'-phosphotransferase, which confers resistance to kanamycin and neomycin.

pCMB1, 5.5 kb, contains the kanamycin resistance gene oriented such that its transcription is in the same direction as that originating from the Trc promoter while pCMB2 contains the kanamycin resistance gene oriented in the opposite direction, such that transcription of the resistance gene and the gene of interest under the control of the Trc promoter result in converging transcripts. Restriction enzyme digests of pCMB1 and pCMB2 using SmaI, HindIII and BamHI+NcoI showed the exact size fragments predicted.

The plasmids pOA5 and pOA6 were transformed into the expression strain of *E. coli* or other suitable organism, preferably the DH5a competent cells. The transformed hosts were grown and protein was induced with IPTG. The time course of induction with pOA5 (FIG. 7B) was similar to that for pOA1 (FIG. 7A) while the levels of OspA produced by pOA6 (FIG. 7C) was several times lower. Identical results to those for pOA5 were obtained using pOA7 and pOA8.

The steps involved in the production and purification of the recombinant full-length ospA are shown schematically in FIGS. 8A to 8C. Specific process conditions are recited therein as set forth in the Examples below.

Following the cell growth step and induction of protein (FIG. 8A), the cells are subjected to freeze-thaw lysis. The lysate is treated with a detergent which is selective for OspA protein solubilization, in preference to other bacterial proteins present in the lysate. Triton X-114 was found to selectively solubilize a 31 kilodalton protein, which was shown to be OspA by immunoblotting.

The invention is not limited to the employment of Triton X-114 but clearly also includes other materials exhibiting a similar selective solubility for OspA as well as the phase separation property under mild conditions referred to below.

Following addition of the selective detergent, the mixture is warmed to a mild temperature elevation of about 35° to 40° C. at which time the solution becomes cloudy as phase separation occurs.

Centrifugation of the cloudy mixture results in separation of the mixture into three phases, namely a detergent phase containing 50% or more of the OspA protein and a small amount (approximately 5 wt %) of the bacterial proteins, an aqueous phase containing the balance of the bacterial proteins and a solid pellet of cell residue. The detergent phase is separated from the aqueous phase and solid pellet.

By the steps of treatment with a selective detergent for OspA and subsequent phase separation of the detergent phase, substantially complete separation of OspA from bacterial proteins is achieved. There remains the final purification of OspA from residual bacterial protein present in the detergent phase.

Final purification of the protein is effected on a chromatography column selective for binding bacterial proteins but not OspA, specifically DEAE-Sephacel, DEAE-Sepharose or other equivalent chromatography material. The detergent phase is loaded onto the column and the flow-through, which contains all the purified OspA protein is collected. The bound fraction contains all the bacterial proteins in the detergent phase. Following further purification using S-Sepharose or equivalent chromatographic column, in addition to being free from contaminating proteins, the flow-through fraction is substantially free from liposaccharide (LPS) as indicated by lack of pyrogenicity, as determined by limulus amebocyte lysate (LAL). The highly purified solution of OspA may be freeze-dried or otherwise processed.

More specifically, plasmid pOA1 was prepared as described above and used to transform E. coli strains BL21 (DE3)(pLysS)(pOA1) and HMS174(DE3)(pLysS)(pOA1). The transformed E. coli was inoculated into LB media with 25 µg/ml of kanamucin sulfate and 25 µg/ml of chloramphenicol at a rate of 12 ml of culture for every liter prepped. The culture was grown overnight in a flask shaker at about 37° C.

The next morning, 10 ml of overnight culture medium was transferred to 1L of LB media containing 25 µg/ml of kanamycin sulfate and the culture was grown in a flask shaker at about 37° C. to a level of OD=0.6 (although growth up to OD=1.5 can be effected), in approximately 3 hours.

To the culture medium was added isopropylthiogalactoside (IPTG) to a final concentration of 0.5 mM and the culture medium was grown for a further two hours at about 37° C. At the end of this period, the culture medium was cooled to about 4° C. and centrifuged at 10000×g for 10 minutes. The supernatant was discarded while the cell pellet was resuspended in 1/10 the volume of PBS. The cell suspension was frozen in liquid nitrogen and may be stored indefinitely at −70° C., if desired.

Following freezing of the cell suspension, the cells were thawed to room temperature (about 20° to 25° C.) which causes the cells to lyse. DNase I was added to the thawed material to a concentration of 1 µg/ml and the mixture was incubated for 30 minutes at room temperature, which resulted in a decrease in the viscosity of the material.

The incubated material was chilled on ice to a temperature below 10° C. and Triton X-114 was added as a 10 wt % stock solution, to a final concentration of 0.3 to 1 wt %. The mixture was kept on ice for 20 minutes. The chilled mixture next was heated to about 37° C. and held at that temperature for 10 minutes.

The solution turned very cloudy as phase separation occurred. The cloudy mixture then was centrifuged at about 20° C. for 10 minutes as 12,000×g, which caused separation of the mixture into a lower detergent phase, an upper clear aqueous phase and a solid pellet. The detergent phase was separated from the other two phases and cooled to 4° C., without disturbing the pellet. Buffer A, namely 50 mM Tris, pH 7.5, 2 mM EDTA and 10 mM NaCl, was added to the cooled detergent phase to reconstitute back to 1/3rd the original volume. The resulting solution may be frozen and stored for later processing as described below or may be immediately subjected to such processing.

A DEAE-Sepharose CL-6B column was prepared in a volume of 1 ml/10 ml of detergent phase and was washed with 2 volumes of Buffer C, namely 50 mM Tris pH 7.5, 2 mM EDTA, 1 M NaCl, 0.3 wt % Triton X-100, and then with 4 volumes of Buffer B, namely 50 mM Tris pH 7.5, 2 mM EDTA, 0.3 wt % Triton X-100.

The detergent phase then was loaded onto the column and the flow-through containing the OspA, was collected. The column was washed with 1 volume of Buffer B and the flow-through again was collected. The combined flow-through was an aqueous solution of purified OspA, which may be frozen for storage.

The column may be freed from bacterial proteins for reuse by eluting with 2 volumes of Buffer C.

Further and final purification of the flow-through from the DEAE-Sepharose column by chromatography on S-Sepharose Fast Flow. The flow-through from the DEAE-Sepharose column first was acidified to pH 4.2 by the addition of 0.1 M citric acid. The S-Sepharose Fast Flow column was washed extensively with Buffer C, adjusted to pH 4.2 with citric acid.

Highly-purified OspA was eluted from the column using Buffer C, adjusted to pH 5.7 with citric acid. The eluate was immediately adjusted back to pH 7.5 by the addition of 2 M Tris base.

The aqueous solution of highly purified OspA obtained by both chromatography procedures was analyzed by Coomassie stained gels and confirmed to contain OspA in highly purified form. The purity of the product produced by the latter chromatography procedure was greater than that formed by the former chromatography procedure, exhibiting very low levels of endotoxin.

Figure 7B:
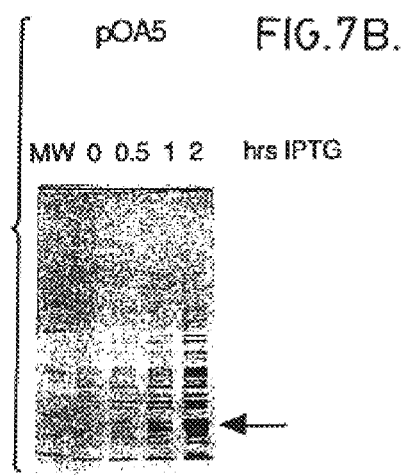
Figure 7C:
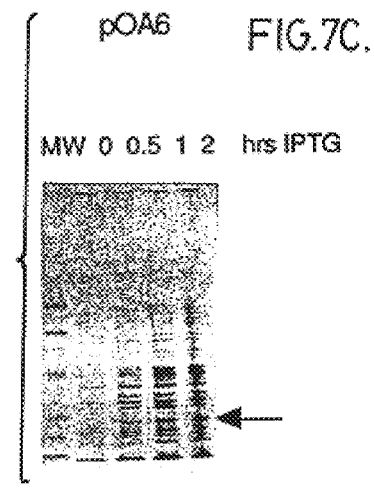
Figure 8A:
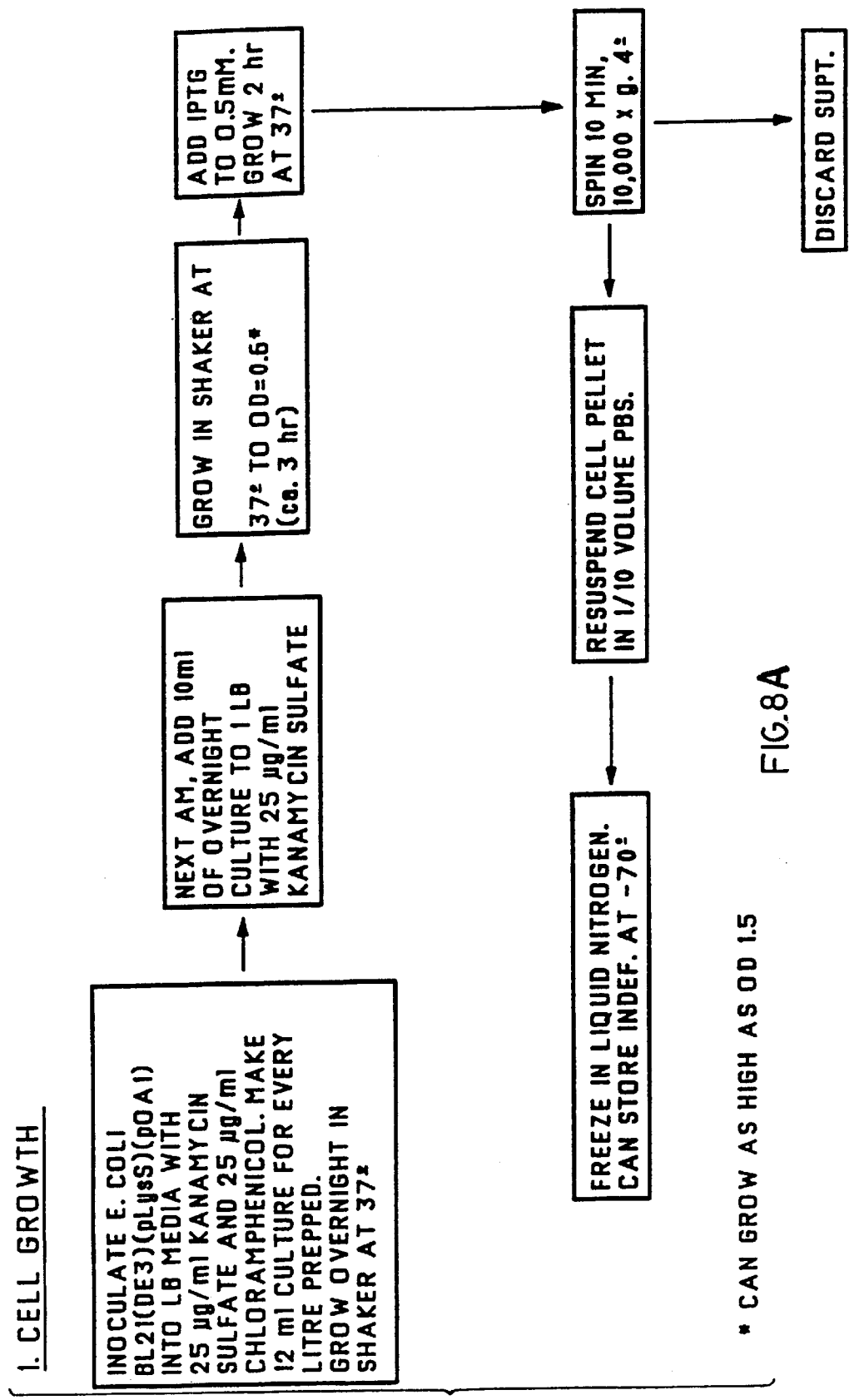
FIGS. 8A, 8B and 8C are flow charts showing, respectively, the cell growth and lysis, the detergent extraction and the purification steps involved in the production and purification of recombinant full-length OspA from *E. coli* in accordance with one embodiment of the invention.
Figure 8B:
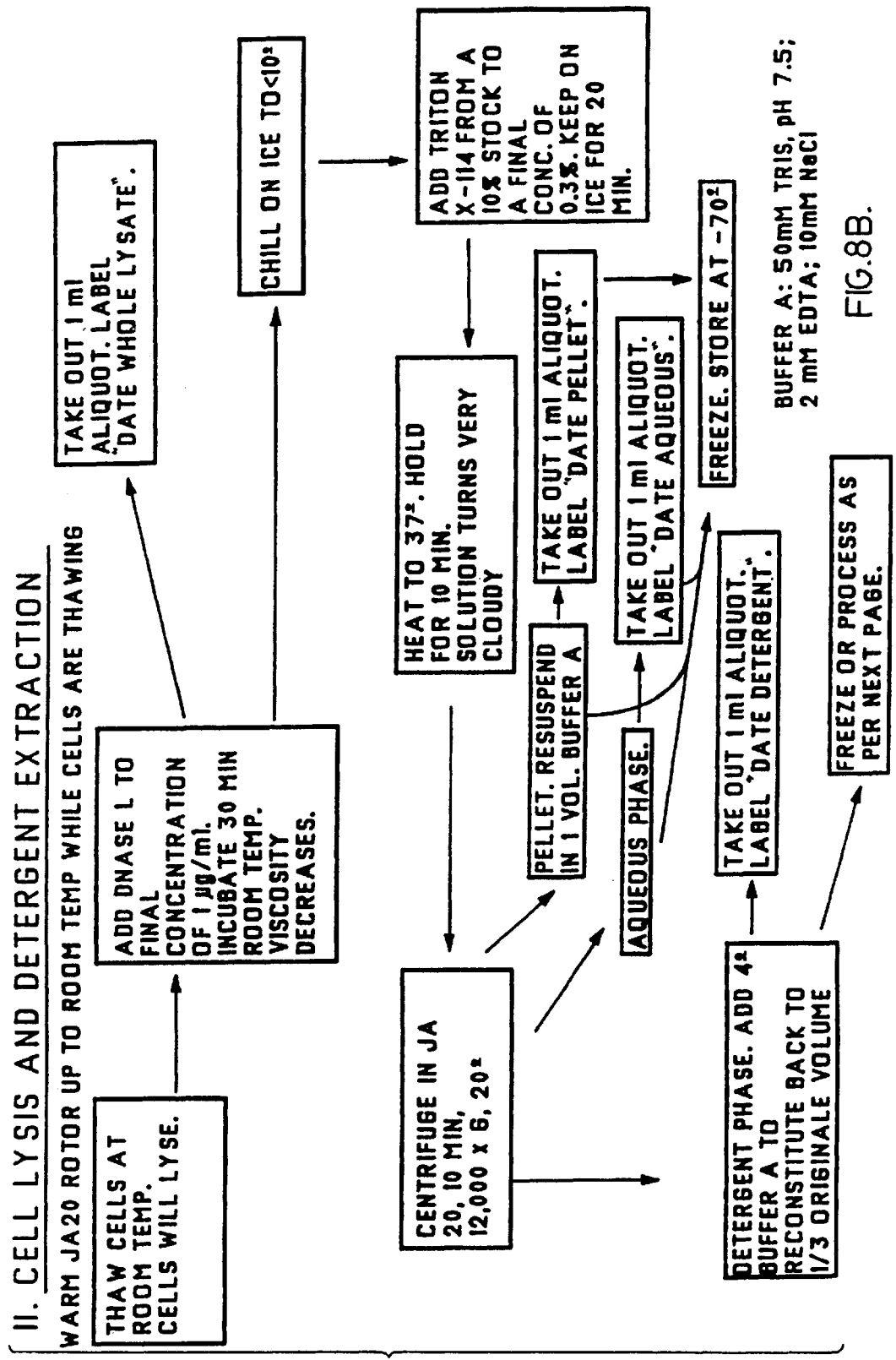
Figure 8C:
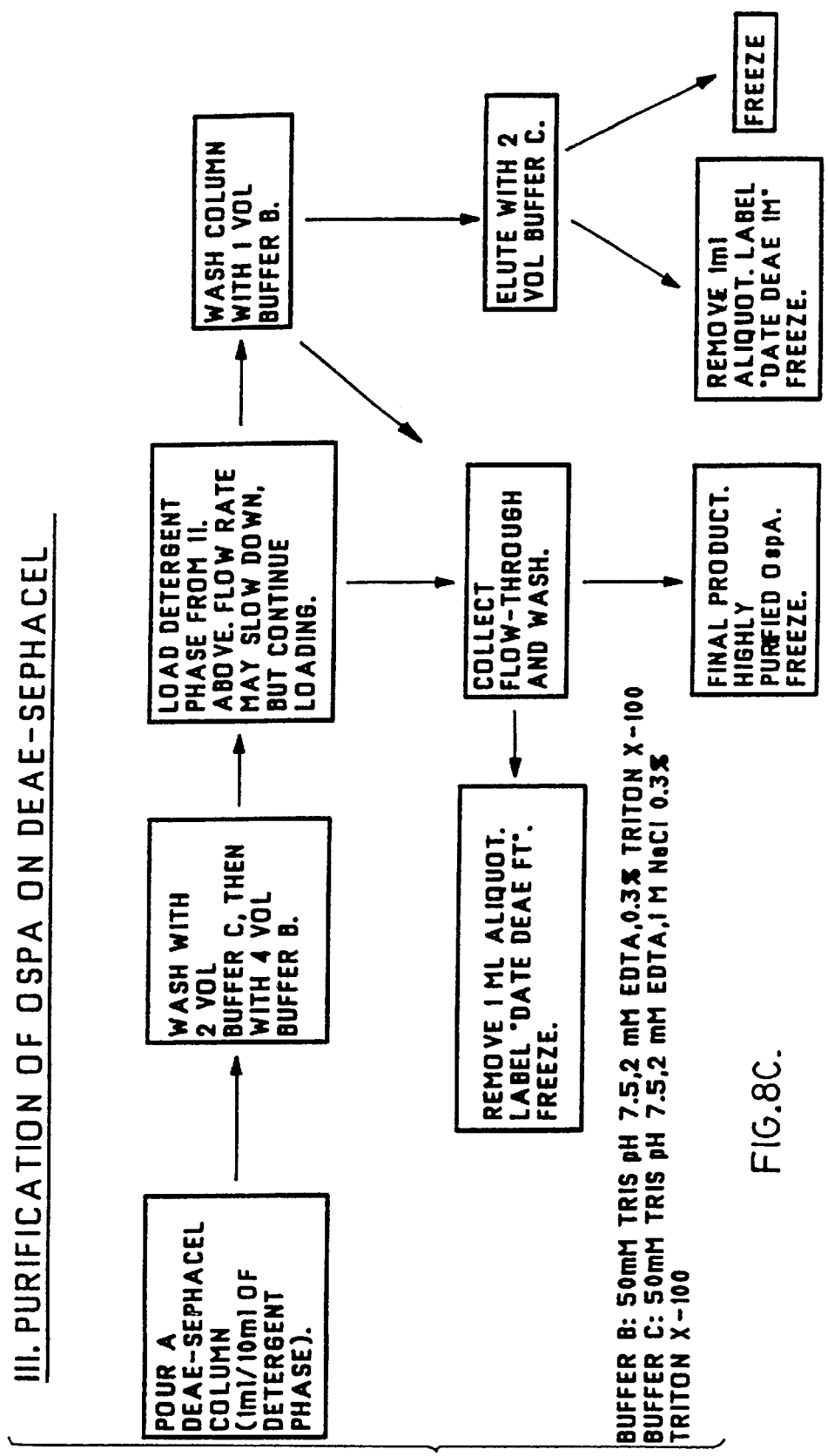
Figure 9:
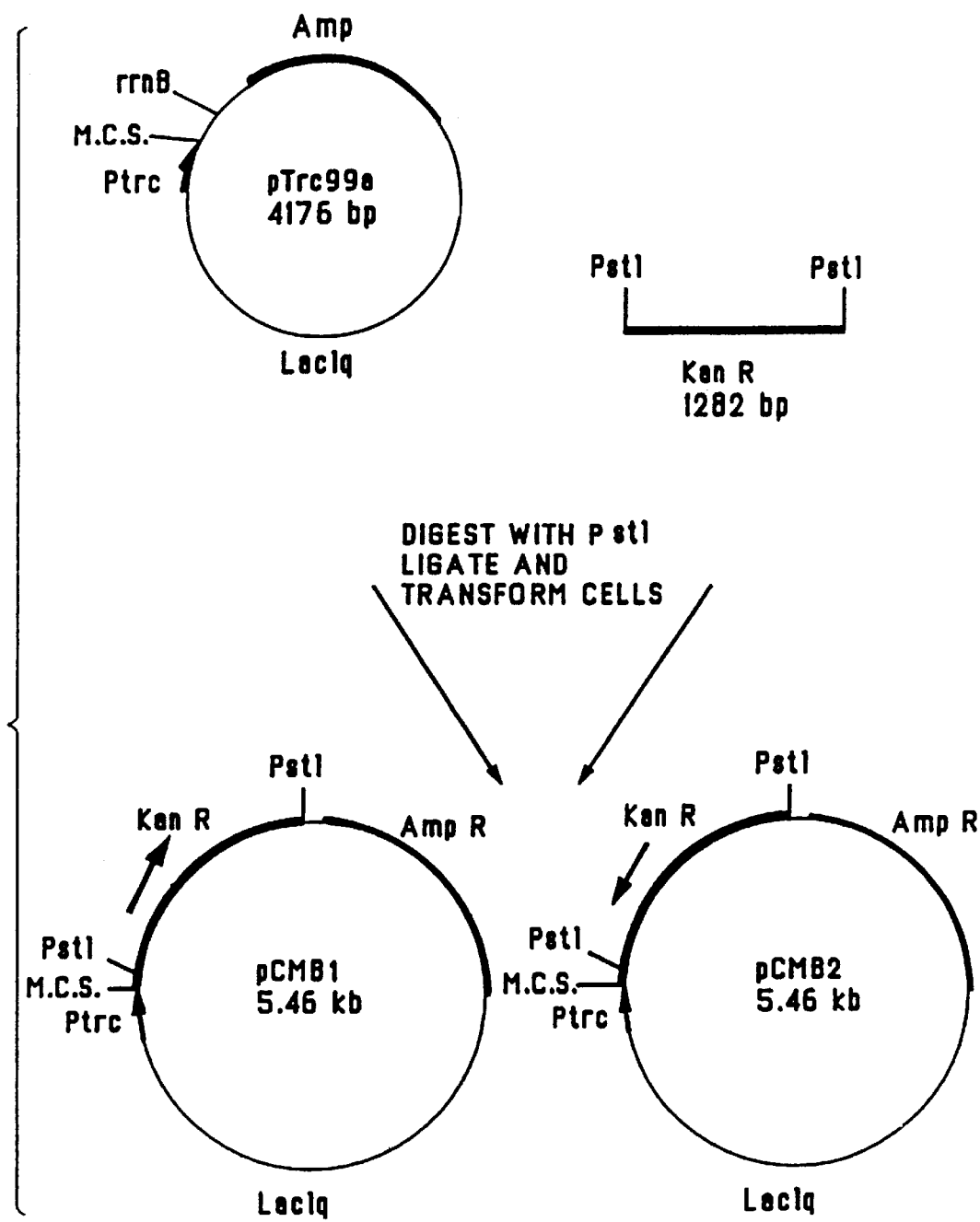
FIG. 9 illustrates the production of plasmids pCMB1 and pCMB2.

Plasmids pOA5 and pOA6 were prepared as described above and used to transform E. coli strain DH5α. The protein expression procedure employed in Example 1 was repeated and the time course expression of the OspA lipoprotein by pOA5 was identical to that observed for pOA1 while OspA expression by pOA6 was found to be several times lower than by pOA5 (FIGS. 7B and 7C). Purification of the OspA protein was continued in pOA5-expressing cells only.

The B31 OspA lipoprotein produced by the Trc expression system in this way was purified following the identical procedure to that described in Example 1, with the exception that 0.1 mg/ml of lysozyme was added to the cell pellet after harvesting and the cells were suspended for 30 minutes at room temperature prior to freezing.

The DEAE-Sepharose column flow through contained OspA lipoprotein in a highly purified form.

The procedures for production of plasmid pOA1 (pET promoter) and pOA5 (TRC promoter) were repeated, as described above, with the cloned ospA gene of Asian strain (Ip90) of B. burgdorferi, to form plasmids pOA8 (Trc promoter) and pOA10 (pET promoter) containing the gene. A restriction digest was performed on these plasmids, which showed all predicted sites to be present.

The procedures also were repeated with the cloned ospA gene of the European strain (ACA1) of B. burgdorferi, to form plasmids pOA7 (Trc promoter) and pOA9 (pET promoter) containing the gene. A restriction digest was performed on these plasmids, which showed all predicted sites to be present.

Growth and induction of the pOA7 and pOA8 expression strains proceeded identically to the pOA5 strain while growth and induction of the pOA9 and pOA10 expression strains proceeded identically to the pOA1 strain.

The ACA1 and Ip90 OspA lipoproteins obtained by these operations were purified identically to the B31 (pOA1) OspA lipoprotein as described above. The DEAE-Sepharose column flow through contained OspA lipoprotein in a highly purified form.

The recombinant lipidated B31 OspA, as prepared above, was used in the formulations the following Examples; however, recombinant OspA from other strains, as herein disclosed, can also be used, especially for domestic animals in Europe or Asia.

Example 2

Recombinant OspA is Protective in Dogs

As repeated in Appel et al., 1993, J. Infect. Dis. 167:651–64, dogs are susceptible to Lyme Disease and there is a concern about the possible transmission from dogs to humans, thereby making it desirable to vaccinate dogs against Lyme Disease (*Borrelia burgdorferi*).

Initial efficacy study: 14 dogs were used in the study: 4 were vaccinated with a low concentration bacterin ($10^7$), 4 were vaccinated with a high concentration bacterin ($10^9$), 4 with an adjuvanted OspA formulation, and 2 were kept as controls. Naturally infected ticks were used to challenge the dogs. All vaccinated dogs were completely protected against infection and demonstrated anti-*B. burgdorferi,* anti-OspA, ELISA antibodies as well as growth inhibiting antibodies. Both controls were infected.

Culture methods: Samples were ground in BSKII medium and inoculated into tubes containing BSKII. Tubes were incubated at 34° C. for 6 weeks. Weekly samples from each tube were screened for evidence of *B. burgdorferi* by dark field microscopy. Any observation of *B. burgdorferi* was scored positive.

Serological methods:

RM ELISA: This is an indirect ELISA. The antigen is a washed sonicate of *B. burgdorferi* strain Bb212 isolated from ticks in France. The conjugate is a goat anti-canine IgG. The substrate is tetramethylbenzidine (TMB). Titers are expressed as the differential O.D. at 450 nm and 620 nm at a dilution of $\frac{1}{100}$ of the serum sample.

Cornell ELISA: This test is performed as described and referenced in Appel et al., supra. It is an indirect ELISA. The antigen is a washed french-press lysate of low passage *B. burgdorferi* isolated from *I. dammini* collected from Westchester County. The conjugate and substrate are the same as above. Titers are expressed as kinetic ELISA units.

OsDA ELISA: This indirect ELISA is performing using a rOspA as the plate antigen. The conjugate is an alkaline phosphatase goat anti-canine IgG. Substrate is signa 104

TABLE 1

Study of efficacy by challenge in dogs - General organization

| VACCINE GROUP | ANIMAL NUMBER | VACCINATION | CHALLENGE | BIOPSY | NECROPSY (+ BIOPSY) |
|---|---|---|---|---|---|
| 1 CONTROLS | 7 14 | — | D42 | D75, D103, D131 | D144 |
| A OspA 2 F31024 | 1 2 8 9 | D0, D21 | D42 | D75, D103, D131 | D137 D139 D137 D139 |
| B Bacterin ($10^7$) 15 A 830 | 3 4 10 11 | D0, D21 | D42 | D74, D102, D130 | D150 D150 D145 D145 |
| C Bacterin ($10^9$) 15 A 850 | 5 6 12 13 | D0, D21 | D42 | D74, D102, D130 | D145 D145 D138 D138 |

*Ixodes daminni* were collected by dragging white flags in forested areas of Westchester County (New-York), one week prior to challenge. Greater than 60% of ticks collected from this area are usually found infected.

Ticks were sorted by stage and sex and maintained at 98% relative humidity until use. At the time of challenge, 15 adult females and 7 adult males were placed on the clipped left flank of each dog under a plastic cap which was kept in place for one week with elastic tape. This time was found sufficient to obtain engorgement of the ticks.

Sample collection: Skin biopsies (4 mm punch biopsies were obtained one, two and three months post challenge and at necropsy, from the site of tick attachment and were cultured for *Borrelia burgdorferi.*

Blood samples were collected weekly from D0 to challenge (D42) then biweekly until necropsy. Serum antibodies were tested as described below.

Necropsy was performed approximately 100 days (97 to 109 after challenge). Muscle and joint capsule material was collected from left and right stifle, front muscle, hind muscle, elbow and shoulder and cultured for *Borrelia burgdorferi.* phosphatase substrate (NA 0200). Titers are expressed as $\log_{10}$ of highest dilution giving an O.D. at 405 nm greater than 0.1.

Growth inhibition assay: This assay is performed as described by SADZIENE & al. (J. Infect. Dis. 1993, 167:165–172). Sera are serially and incubated with *B. burgdorferi* organisms for 62–66 hours in the presence of two hemolytic units of fresh guinea pig complement. By that time, the phenol red color indicator in the BSKII growth medium has changed from pink to yellow in the wells where spirochetes exist. Three wells from each side of this point are examined by dark field microscopy to verify the dilution where the viable cells have decreased by 90%. Titers are expressed as the $\log_{10}$ of this dilution.

Results

Skin biopsies: Results are presented in Table 2. Control dogs were found positive on all samples. No positive samples were found in any of the 12 vaccinated dogs.

TABLE 2

| VACCINE GROUP | ANIMAL NUMBER | BIOPSY (month post challenge)* 1 | 2 | 3 | 3.5** |
|---|---|---|---|---|---|
| 1 controls | 7 | + | + | + | + |
|  | 14 | + | + | + | + |
| A OspA 2 F 31024 | 1 | – | – | – | – |
|  | 2 | – | – | – | – |
|  | 8 | – | – | – | – |
|  | 9 | – | – | – | – |
| B Bacterin ($10^7$) 15 A 830 | 3 | – | – | – | – |
|  | 4 | – | – | – | – |
|  | 10 | – | – | – | – |
|  | 11 | – | – | – | – |
| C Bacterin ($10^9$) 15 A 850 | 5 | – | – | – | – |
|  | 6 | – | – | – | – |
|  | 12 | – | – | – | – |
|  | 13 | – | – | – | – |

*Cultures examined weekly for 6 weeks following inoculation
**Biopsy performed at challenge Necropsy—Culture results: These results are detailed in Table 3. Both control dogs gave positive cultures from various organs on either side. Rate of isolation does not seem more frequent on left side (challenge side) than on right side.

Serology

RM ELISA: Results are presented in Table 4.

Following vaccination with either the OspA vaccine or the bacterins, most had a noticeable increase in titers after one injection with a significant booster effect from the second vaccination.

Following challenge titers of vaccinated dogs remained stable but control dogs increased gradually over a two-month period.

TABLE 3

Lyme Disease Vaccine
Study of efficacy by challenge in dogs
Culture results from tissues collected at necropsy

| VACCINE GROUP | ANIMAL NUMBER | STIFLES LEFT | STIFLES RIGHT | MUSCLE LEFT FRONT | MUSCLE LEFT HIND | MUSCLE RIGHT FRONT | MUSCLE RIGHT HIND | ELBOW LEFT | ELBOW RIGHT | SHOULDER LEFT | SHOULDER RIGHT |
|---|---|---|---|---|---|---|---|---|---|---|---|
| 1 CONTROLS | 7 | – | – | + | – | + | – | + | – | + | + |
|  | 14 | – | + | – | – | + | – | + | + | + | + |
| A OspA 2 F 31024 | 1 | – | – | – | – | – | – | – | – | – | – |
|  | 2 | – | – | – | – | – | – | – | – | – | – |
|  | 8 | – | – | – | – | – | – | – | – | – | – |
|  | 9 | – | – | – | – | – | – | – | – | – | – |
| B BACTERIN ($10^7$) 15 A 830 | 3 | – | – | – | – | – | – | – | – | – | – |
|  | 4 | – | – | – | – | – | – | – | – | – | – |
|  | 10 | – | – | – | – | – | – | – | – | – | – |
|  | 11 | – | – | – | – | – | – | – | – | – | – |
| C BACTERIN ($10^9$) 15 A850 | 5 | – | – | – | – | – | – | – | – | – | – |
|  | 6 | – | – | – | – | – | – | – | – | – | – |
|  | 12 | – | – | – | – | – | – | – | – | – | – |
|  | 13 | – | – | – | – | – | – | – | – | – | – |

TABLE 4

Lyme Disease Vaccine
Study of efficacy by challenge in dogs
RM ELISA serology (titers expressed as O.D. by serum at 1/100)

| VACCINE GROUP | ANIMAL NUMBER | DAY POST-VACCINATION 0* | 8 | 14 | 21* | 28 | 35 | 42** | 61 | 75 | 89 | 103 | 116 |
|---|---|---|---|---|---|---|---|---|---|---|---|---|---|
| 1 CONTROLS | 7 | 0.16 | ND | 0.09 | 0.10 | 0.08 | 0.07 | 0.06 | 0.15 | 0.16 | 0.28 | ND | 0.44 |
|  | 14 | 0.06 | ND | 0.07 | 0.08 | 0.07 | 0.15 | 0.10 | 0.11 | 0.14 | 0.23 | ND | 0.33 |
|  | Mean | 0.11 |  | 0.08 | 0.09 | 0.08 | 0.11 | 0.08 | 0.13 | 0.15 | 0.26 |  | 0.39 |
|  | St$^d$ deviation | 0.07 |  | 0.01 | 0.01 | 0.01 | 0.06 | 0.03 | 0.03 | 0.01 | 0.04 |  | 0.08 |
| A OspA | 1 | 0.09 | ND | 0.16 | 0.20 | 0.69 | 0.53 | 0.50 | 0.51 | 0.44 | 0.47 | 0.43 | 0.48 |
|  | 2 | 0.09 | ND | 0.10 | 0.12 | 0.44 | 0.36 | 0.31 | 0.27 | 0.28 | 0.22 | 0.37 | 0.34 |

TABLE 4-continued

Lyme Disease Vaccine
Study of efficacy by challenge in dogs
RM ELISA serology (titers expressed as O.D. by serum at 1/100)

| VACCINE GROUP | ANIMAL NUMBER | 0* | 8 | 14 | 21* | 28 | 35 | 42** | 61 | 75 | 89 | 103 | 116 |
|---|---|---|---|---|---|---|---|---|---|---|---|---|---|
| 2 F | 8 | 0.08 | ND | 0.11 | 0.15 | 0.60 | 0.58 | 0.56 |  | 0.45 | 0.52 | 0.47 | 0.47 |
| 31024 | 9 | 0.14 | ND | 0.18 | 0.16 | 0.47 | 0.41 | 0.44 | 0.50 | 0.40 | 0.38 | 0.40 | 0.45 |
|  | Mean | 0.10 |  | 0.14 | 0.16 | 0.55 | 0.47 | 0.45 | 0.47 | 0.39 | 0.40 | 0.42 | 0.44 |
|  | St$^d$ deviation | 0.03 |  | 0.04 | 0.03 | 0.12 | 0.10 | 0.11 | 0.14 | 0.08 | 0.13 | 0.04 | 0.06 |
| B | 3 | 0.09 | 0.12 | 0.19 | 0.32 | 0.58 | 0.50 | 0.50 | 0.53 | 0.50 | 0.51 | 0.60 | ND |
| BACTERIN | 4 | 0.08 | 0.09 | 0.21 | 0.29 | 0.47 | 0.40 | 0.41 | 0.47 | 0.44 |  | ND | ND |
| ($10^7$) | 10 | 0.05 | 0.08 | 0.13 | 0.27 | 0.51 | 0.56 | 0.53 | 0.44 | 0.42 | 0.40 | 0.38 | ND |
| 15 A | 11 | 0.07 | 0.09 | 0.14 | 0.20 | 0.42 | 0.44 | 0.41 | 0.38 | 0.31 | 0.34 | 0.37 | ND |
| 830 | Mean | 0.07 | 0.10 | 0.17 | 0.27 | 0.50 | 0.48 | 0.46 | 0.46 | 0.44 | 0.42 | 0.45 |  |
|  | St$^d$ deviation | 0.02 | 0.02 | 0.04 | 0.05 | 0.07 | 0.07 | 0.06 | 0.06 | 0.04 | 0.09 | 0.13 |  |
| C | 5 | 0.10 | 0.16 | 0.21 | 0.27 | 0.51 | 0.44 | 0.52 | 0.42 | 0.37 | 0.45 | 0.36 | ND |
| BACTERIN | 6 | 0.13 | 0.16 | 0.30 | 0.33 | 0.55 | 0.45 | 0.44 | 0.36 | 0.34 | 0.43 | 0.22 | ND |
| ($10^9$) | 12 | 0.06 | 0.13 | 0.19 | 0.19 | 0.46 | 0.31 | 0.35 | 0.24 | 0.21 | 0.23 | 0.43 | ND |
| 15 A | 13 | 0.03 | 0.09 | 0.27 | 0.28 | 0.60 | 0.63 | 0.56 | 0.45 | 0.50 | 0.49 | 0.36 | ND |
| 850 | Mean | 0.08 | 0.14 | 0.24 | 0.27 | 0.53 | 0.48 | 0.47 | 0.37 | 0.36 | 0.40 | 0.10 |  |
|  | St$^d$ deviation | 0.04 | 0.03 | 0.05 | 0.06 | 0.06 | 0.10 | 0.09 | 0.09 | 0.12 | 0.12 |  |  |

Cornell ELISA: Results are present in Table 5.

The pattern antibody increase is almost identical to that obtained with RM ELISA.

All vaccinates show a significant increase in titers after one injection and a booster effect of the second vaccination. Following challenge, titers remain stable.

Controls show a gradual increase in titers over a 3-month period.

OSpA ELISA: Results are presented in Table 6.

Both bacterins induce similar levels of anti-OspA antibody.

The OspA vaccine induces a significant homologous antibody response.

The pattern is similar to the whole cell lysate ELISA: increase after one injection, boost with second injection.

Grown inhibition: Results are presented in Table 6.

Both bacterins and the OspA vaccine induced high levels of *B. burgdorferi* inhibiting antibodies in all dogs vaccinated.

TABLE 5

Lyme Disease Vaccine
Study of efficacy by challenge in dogs
RM ELISA serology (titers expressed as K ELISA units)

| VACCINE GROUP | ANIMAL NUMBER | 0* | 8 | 14 | 21* | 28 | 35 | 42** | 61 | 75 | 89 | 103 | 116 | 131 | 141 |
|---|---|---|---|---|---|---|---|---|---|---|---|---|---|---|---|
| 1 | 7 | 38 | ND | 37 | 41 | 38 | 44 | 43 | 68 | 131 | 218 | 327 | 361 | 437 | 388 |
| CONTROLS | 14 | 25 | ND | 24 | 26 | 30 | 40 | 34 | 62 | 183 | 234 | 295 | 365 | 393 | 386 |
|  | Mean | 32 |  | 31 | 35 | 34 | 42 | 39 | 65 | 157 | 226 | 311 | 363 | 416 | 387 |
|  | St$^d$ deviation | 9 |  | 9 | 9 | 6 | 3 | 6 | 4 | 37 | 11 | 23 | 3 | 30 | 1 |
| A | 1 | 41 | ND | 236 | 381 | 583 | 585 | 561 | 541 | 51 | 521 | 498 | 471 | 452 | 437 |
| OspA | 2 | 68 | ND | 73 | 142 | 525 | 498 | 485 | 353 | 257 | 216 | 204 | 194 | 174 | ND |
| 2 F | 8 | 37 | ND | 151 | 287 | 567 | 613 | 593 | 569 | 560 | 569 | 542 | 471 | 455 | 428 |
| 31024 | 9 | 40 | ND | 304 | 325 | 571 | 570 | 566 | 560 | 488 | 482 | 446 | 404 | 360 | ND |
|  | Mean | 47 | 46 | 191 | 284 | 562 | 567 | 551 | 506 | 455 | 447 | 423 | 385 | 360 |  |
|  | St$^d$ deviation | 14 | 25 | 101 | 102 | 25 | 49 | 40 | 103 | 135 | 158 | 151 | 131 | 132 |  |
| B | 3 | 74 | 74 | 290 | 453 | 616 | 636 | 611 | 603 | 579 | 582 | 566 | 573 | 573 | 580 |
| BACTERIN | 4 | 56 | 61 | 221 | 315 | 601 | 583 | 583 | 540 | 539 | 466 | 505 | 487 | 546 | 542 |
| 10($^7$) | 10 | 6 | 26 | 113 | 292 | 567 | 592 | 556 | 566 | 442 | 504 | 436 | 465 | 420 | 451 |
| 15 A | 11 | 15 | 23 | 197 | 409 | 601 | 565 | 547 | 501 | 494 | 426 | 430 | 435 | 442 | 461 |
| 850 | Mean | 38 | 46 | 205 | 367 | 596 | 594 | 574 | 553 | 514 | 495 | 484 | 490 | 495 | 509 |
|  | St$^d$ deviation | 33 | 25 | 73 | 76 | 21 | 30 | 29 | 43 | 59 | 66 | 64 | 59 | 76 | 63 |
| C | 5 | 59 | 95 | 211 | 347 | 636 | 644 | 628 | 577 | 556 | 542 | 501 | 509 | 488 | 474 |
| BACTERIN | 6 | 79 | 125 | 355 | 383 | 628 | 625 | 596 | 504 | 485 | 518 | 484 | 510 | 481 | 360 |
| ($10^9$) | 12 | 11 | 69 | 234 | 292 | 562 | 553 | 521 | 404 | 317 | 325 | 304 | 315 | 283 | 284 |
| 15 A | 13 | 13 | 41 | 356 | 471 | 545 | 546 | 531 | 516 | 504 | 484 | 461 | 463 | 444 | 439 |
| 850 | Mean | 41 | 83 | 289 | 373 | 593 | 592 | 569 | 500 | 466 | 467 | 438 | 449 | 424 | 389 |
|  | St$^d$ deviation | 34 | 36 | 77 | 75 | 46 | 50 | 52 | 72 | 103 | 98 | 90 | 92 | 96 | 85 |

*D0, D21: Vaccination
**D42: First day of challenge
ND: Not Done

TABLE 6

Lyme Disease Vaccine
Study of efficacy by challenge in dogs OspA ELISA and growth inhibition (titers expressed as log10 of endpoint dilution,

| VACCINE GROUP | ANIMAL NUMBER | ELISA D0 | ELISA D21 | ELISA D42 | I.C. D42 |
|---|---|---|---|---|---|
| 1 CONTROLS | 7 | 1.7 | 1.7 | 1.7 | <0.9 |
| A | 1 | 2.3 | 2.9 | >3.8 | 3.3 |
| OSPA | 2 | 1.7 | 2.0 | 3.2 | 3.0 |
| 2 F 31024 | 8 | 1.7 | 2.9 | 3.8 | 3.5 |
|  | 9 | 2.0 | 2.9 | >3.8 | 2.7 |
| B | 3 | 2 | 2.9 | >3.8 | 3.6 |
| BACTERIN | 4 | 2 | 2.3 | >3.8 | 2.6 |
| ($10^7$) | 10 | 1.7 | 2.3 | >3.8 | 2.7 |
| 15 A 830 | 11 | 1.7 | 2.9 | >3.8 | 2.7 |
| C | 5 | 2.3 | 2.6 | >3.8 | 3 |
| BACTERIN | 6 | 2 | 2.6 | 3.2 | 2.9 |
| ($10^9$) | 12 | 2.3 | 2.3 | 3.2 | 2.7 |
| 15 A 850 | 13 | 2 | 2.9 | >3.8 | 3 |

Challenge

The challenge method used has a variety of advantages over other published challenged methods based on needle administration of *B. burgdorferi*.

Challenge vector and route mimic the natural situation.

Infection can be traced in vivo by skin biopsies.

Furthermore, the challenge (U.S. origin ticks) can be considered heterologous for the two bacterins (French strain).

The lack of clinical signs is a limitation but, as described in Appel et al., this is totally expected in dogs of this age.

Under these conditions, the results—i.e.: all controls infected and none of the 12 vaccinates infected—demonstrate that both the bacterins at high or low concentration, and the OspA vaccine completely protected the dog against challenge.

Serology

The three vaccines gave similar results by all methods used: increase after one injection, booster effect of the second injection.

It is interesting to note the high degree of correlation between the two lysate ELISA's used (RM ELISA, Cornell ELISA) in spite of a difference in the strain used for antigen production and in expression of results (FIG. 3) ($r^2=0.86$, F==935, $\alpha=0.001$).

It is also important to note that the antibodies induced by vaccination:

React strongly with OspA, the major outer membrane protein of *B. burgdorferi*,

Strongly inhibit growth of *B. burgdorferi*.

Conclusion

Bacterins containing a low dose ($10^7$) or high dose ($10^9$) of killed cells of *B. burgdorferi* completely protected dogs challenged by a natural route (tick exposure).

The same results were obtained with the OspA adjuvanted vaccine.

All vaccines induced a significant and similar increase in antibody titers which recognized the OspA lipoprotein and inhibited growth of *B. burgdorferi*.

Duration of Immunity Study

Thirty-three (33) Beagles were divided into two groups. The first group (20 dogs) received two SC doses of a monovalent vaccine (10 μg/dose OspA recombinant B31 as prepared in Example 1) at a 3 or 4 week vaccination interval. The second group was untreated (13 dogs). All dogs were tick-challenged 5 to 6 months after the second vaccination. Antibody levels were determined at regular intervals by ELISA. Vaccine efficacy was assessed by spirochete reisolation at one and two months postchallenge. Dogs were also monitored for clinical signs indicative of canine Lyme Disease (LD).

Summary

Safety: No adverse local or generalized reactions were found following injection of vaccine.

| GROUP | # DOGS | POSTVACCINAL SEROCONVERSION | POSTCHALLENGE RESULTS Clinical Signs | Skin Biopsy at 2 mos./ Spirochete Reisolation |
|---|---|---|---|---|
| Ly | 20 | 19/20 = 95% | 1/20 = 5% | 2/20 = 10% |
| Controls | 13 | 0/13 = 0% | 5/13 = 39% | 13/13 = 100% |

The monovalent Ly OspA Vaccine:
*elicits protection against canine LD as assessed by both spirochete reisolation and clinical signs.
*this protection response is effective at least five months post vaccination.
*protects against spirochete infection (90%) and clinical signs after a natural challenge.

Animals

Thirty-three Beagle puppies (either sex; nine to ten weeks of age; negative for Lyme and Leptospira vaccination) were obtained from Ridglan Farms (Mount Horeb, Wis.). The puppies were divided randomly into two groups and vaccinated.

| GROUP | DOG | ROUTE | TREATMENT PROTOCOL |
|---|---|---|---|
| 1 | 10 | SC | Ly; 4 week interval |
| 2 | 10 | SC | Ly; 3 week interval |
| 3 | 13 |  | Untreated controls |

Vaccine Preparation

The OspA monovalent vaccine (designated Ly) was prepared by diluting a stock concentration of the B31 OspA purified protein produced as in Example 1. The concentration of the stock was 465 μg OspA/ml. The Lyme vaccine was produced by diluting the stock concentration in sterile diluent to a concentration of 10 μg/ml of OspA and aliquoting the vaccine into single and multiple use vials (1 ml and 10 ml respectively). The vaccine was tested satisfactorily for sterility.

Vaccination Protocol

Dogs received two doses of vaccine (1 ml/dose) administered subcutaneously at an interval of three (Group 1) or four weeks (Group 2). Signs of anaphylaxis, including difficulty in breathing, itching, and edema, were monitored for the initial 15 minutes following injection. Additionally, the dogs were observed continuously for the first hour after vaccination, and then at regular intervals during the 14 days after each injection. Signs monitored included swelling, pain, tenderness, and scratching at the injection site. Prior to administration of the second injection, the site of the primary vaccination was palpitated for swelling and tenderness.

Serology

Blood was taken for titer determination before each vaccination and at monthly intervals thereafter. OspA titers were determined by ELISA.

Challenge

All dogs were challenged with B. burgdorferi using naturally infected ticks, according to the challenge procedure of Appel et al. The interval between final vaccination and challenge was 24 weeks for Group 1 and 21 weeks for Group 2. The ticks were gathered in Westchester county, N.Y., an area endemic for Lyme Disease, and the challenge was conducted according to the procedure of Appel et al. The Borrelia burgdorferi infection rate of these ticks was 60%.

Skin Biopsy and Spirochete Reisolation

All dogs were biopsied at one and two months postchallenge. The skin around the site of tick attachment was shaved, prepped with Betadine surgical scrub, anesthetized with 2% lidocaine injected intradermally, and punch-biopsied using a Baker Skin Punch. Skin samples were placed in tubes containing culture medium (BSK media with heat-inactivated rabbit serum and antibiotics) and transported to the laboratory. Tubes were supplemented with additional media and placed in a candle jar. The jar was incubated for six weeks. Tubes were examined weekly for the presence of spirochetes, using a dark field microscope. At least ten fields were examined using a 40× objective before the sample was considered negative.

Clinical Signs and Symptoms

Clinical signs of canine Lyme Disease (LD) were not expected following infection, due to the variable nature of the disease, therefore efficacy of the vaccines was assessed primarily by the reisolation of Sorrelia burgdorferi spirochetes from skin biopsy samples. However, all dogs were monitored for appearance of signs indicative of LD. Pain and tenderness, temperature, lameness, ataxia, depression, and anorexia are among the signs for which these dogs were monitored. Only an estimated 10–15% of dogs naturally infected with Borrelia burgdorferi exhibited clinical signs.

Results

Vaccine Safety

All vaccinated dogs were monitored for adverse reactions (including anaphylaxis) for the first fifteen minutes following vaccination and two weeks following each vaccination. No adverse reactions were found at any time following either injection of the Lyme monovalent vaccine. Additionally no swelling, pain, tenderness, or itching was found at the injection site during the two week period following vaccination. Antibody Titers (See Table 7):

Antibody to OspA was determined by ELISA. Table 7 lists the ELISA values. At the time of tick challenge, most of the dogs vaccinated with the monovalent vaccine (10 μg OspA) still exhibited significant OspA antibody titers. One dog, FAS<failed to mount a significant antibody response to OspA. Spirochete Reisolation (See Table 7):

Skin biopsies were performed for all dogs at one and two months postchallenge. Biopsies were cultures for six weeks and examined for spirochete reisolation. Spirochetes were reisolated from seven of twelve control dogs at the first biopsy (58%). One sample could not be read because it was lost after five weeks in culture, due to contamination. All 13 samples (100%) from control dogs were positive for spirochetes by the second biopsy date.

Results show that only two dogs vaccinated with the monovalent Lyme vaccine (HVT and DXT) were positive for spirochetes; a reisolation rate of 10%.

Clinical Signs of Canine Lyme Disease (See Tables 6 and 7)

Five months postchallenge, five of the 13 unvaccinated controls (39%) have experienced episodes attributable to LD; two dogs (HXT and JCT) have had multiple episodes. One of the twenty vaccinates (5.0%) also experienced a single episode of lameness.

Discussion

Vaccine efficacy was assessed by determining the ability of the vaccine to prevent both spirochete dissemination and clinical signs in short term and duration of immunity trials. LD in dogs often does not result in the appearance of clinical disease (Levy and Magnarelli, 1992, JAVMA, 200: 344–347), therefore in addition to the reporting of clinical signs, vaccine efficacy was based upon the ability of the experimental preparations to prevent spirochete proliferation, as assessed by the reisolation of spirochetes from skin biopsies. Spirochete reisolation is the most important, and most consistent, parameter to consider when assessing the efficacy of a vaccine. If vaccination decreases or eliminates this dissemination, the animal will not develop clinical signs. The Ly vaccine was shown to protect >90% of recipients against spirochete proliferation in the short term efficacy trial as discussed above. In this duration of immunity (DOI) study, with dogs challenged 5 to 6 months after vaccination, 100% of the untreated controls were positive for spirochetes by the second biopsy date. In contrast spirochetes were reisolated from only two of the vaccinates (10%).

Dogs were also observed for clinical signs resulting from infection. Observations were reported by animal technicians blinded as to the vaccination status of each dog. In the short term efficacy study discussed above 25% of the untreated controls demonstrated signs typical of canine Lyme disease (LD), mainly lameness, while no vaccinate was observed with signs. In this DOI study six of the dogs have shown such signs; five are unvaccinated controls (39%) and one dog was a vaccinate (5%). The first episode of lameness was noted approximately two months post-challenge; since then two of the untreated dogs (JRT and IAT) exhibited recurring episodes.

One vaccinate, HPS, was reported with swelling and slight lameness in the front right foot approximately 2 months after challenge. The animal was never positive for spirochete isolation, although cultures from that dog were examined specifically with the lameness episode in mind. It is possible that this episode was not the result of canine LD, but was attributable to other causes (trauma, etc.). However, the dog was listed as positive for clinical signs in order to provide as stringent a test as possible.

Antibody titer results show that all but one of the dogs (FAS) vaccinated with the monovalent vaccine had seroconverted after vaccination, as determined by a difference in prebleed and prechallenge titers of at least two dilutions.

This represents a seroconversion rate of 95%. By the time of challenge all but two vaccinates (FAS and HVT) still exhibited significant titers. None of the control dogs showed a sustained increase in OspA antibody levels, although three controls (HXT, JBT, and JIT) did have low levels of antibody reported from the prechallenge bleed.

The safety of the Ly monovalent vaccine is also demonstrated by the results of this experiment. No adverse effects were noted at the time of vaccination, or in the two week period following each injection. The 10 µg OspA/dose was well tolerated by all of the puppies. Because this vaccine contains no adjuvant, even the mild and transient granulomatous response characteristic of vaccination with most adjuvanted preparations was absent.

Conclusion

The monovalent vaccine, containing 10 µg OspA/dose:

is safe in 9 to 10 week old puppies.

is very antigenic and induces a seroconversion in 95% of recipients.

elicits an immune response which protects vaccinates against spirochete infection (90%) and clinical signs five to six months after vaccination, when 100% of the controls demonstrate spirochete infection and 39% exhibit clinical signs following tick challenge.

This Example also demonstrates that the inventive vaccine is protective for an entire Lyme Disease season.

TABLE 8

Clinical Signs of Canine Lyme Disease in Five-Month Challenge

| Dog # | Group | Remarks |
| --- | --- | --- |
| HXT | Control | Lameness (all limbs), ataxia, depressed, anorexic |
| | | Lame (Left Front) |
| | | Lame (Left Front); All episodes resolved spontaneously |
| JBT | Control | Lame (Left Front), Episode resolved spontaneously |
| JCT | Control | Lame (Rear Legs); resolved spontaneously |
| | | Lame (Right Front); resolved spontaneously |
| JJT | Control | Lame (Right Front); resolved spontaneously |
| JYS | Control | Lame (Left Front); resolved spontaneously |
| HPS | VAX | Limping (Right Front); resolved spontaneously |

Dogs were vaccinated with 1 ml Ly vaccine SQ at a three or four week interval. Challenge was at 5 to 6 months. Dogs were monitored blindly for clinical signs by animal technicians.

TABLE 7

Results of Antibody Titers to OspA, Spirochete Reisolation and Clinical Signs in the Duration of Immunity Trial (DOI).

| Vaccine | Dogs | Month 0 Prebleed | Month 1 | Month 2 | Month 3 | Month 4 | Month 5 | Month 6 Prechall. | Spirochete Biopsy 1 | Reisolation Biopsy 2 | Clinical Signs |
| --- | --- | --- | --- | --- | --- | --- | --- | --- | --- | --- | --- |
| Vaccinated | DVT | 50 | 200 | 1600 | 1600 | 800 | 800 | 800 | − | − | |
| | DWT | <25 | 25 | 200 | 200 | 50 | 50 | 200 | | | |
| | DXT | 50 | 100 | 200 | 50 | 50 | 50 | 50 | + | + | |
| | EBT | <25 | 50 | 800 | 800 | 100 | 100 | 200 | | | |
| | ESC | <25 | 100 | 1600 | 800 | 400 | 200 | 200 | − | − | |
| | EDS | <25 | 800 | 800 | 400 | 200 | 100 | 100 | − | | |
| | EHS | <25 | 100 | 50 | 50 | 50 | 25 | 50 | − | − | |
| | EIS | 200 | 100 | 200 | 100 | 25 | 25 | 50 | − | | |
| | FAS | <25 | <25 | 25 | 25 | <25 | <25 | <25 | − | − | |
| | FJS | <25 | <25 | 200 | 200 | 200 | 100 | 200 | | | |
| | FKS | <25 | <25 | 6400 | 800 | 400 | 400 | − | − | | |
| | HPS | <25 | <25 | 8400 | 400 | 100 | 100 | 100 | − | − | + |
| | HVT | <25 | <25 | 800 | 50 | 50 | <25 | <25 | + | + | |
| | HWT | <25 | <25 | 400 | 50 | 255 | 255 | 50 | | | |
| | ICS | <25 | <25 | 12800 | 1600 | 400 | 400 | 1600 | − | | |
| | IDS | 50 | <25 | 1600 | 400 | 100 | 200 | 400 | | | |
| | IHT | <25 | <25 | 12800 | 1600 | 400 | 400 | 1600 | − | − | |
| | ?S | <25 | <25 | 12800 | 800 | 200 | 400 | 1600 | | | |
| | LJS | <25 | <25 | 6400 | 1600 | 400 | 800 | 800 | − | − | |
| | IPT | <25 | <25 | 12800 | 800 | 600 | 1600 | | | | |
| Non-Treated | HXT | <25 | <25 | <25 | <25 | 25 | 50 | 100 | − | + | + |
| | IQS | <25 | <25 | 50 | <25 | 25 | <25 | 25 | | | |
| | IVS | <25 | <25 | <25 | 25 | 50 | 50 | 50 | ‡ | + | |
| | JES | 25 | <25 | <25 | <25 | 25 | <25 | 25 | + | + | |
| | ITS | 25 | <25 | <25 | <25 | <25 | <25 | <25 | + | + | |
| | IUS | <25 | <25 | <25 | <25 | <25 | <25 | <25 | + | + | |
| | JBT | 50 | <25 | <25 | <25 | <25 | <25 | 100 | − | + | + |
| | JCT | 200 | <25 | 200 | 50 | 25 | 50 | 50 | | | + |
| | JIT | <25 | <25 | 25 | <25 | <25 | 100 | 100 | + | + | |
| | LIT | <25 | <25 | 25 | <25 | <25 | 25 | <25 | − | | + |
| | JKS | 25 | <25 | 25 | <25 | <25 | 25 | <25 | | | |
| | JYS | <25 | <25 | 50 | <25 | 25 | 25 | 50 | − | + | + |

All dogs were biopsied at 1, 2 and 3 months postchallenge (acc Materials and Methods). Skin samples were culture in BSK media (supplemented with antibiotics and 10% rabbit serum) for 6 weeks; tubes were examined weekly using a dark field microspace, with at least then fields examined before sample was considered an negative. ‡ Sample lost due to contamination.

Example 3

Formulation of Combination Compositions Displaying No Efficacy Interference

This example demonstrates that there is no interference between Canine Distemper-Adenovirus Type 2-Coronavirus-Parainfluenza-Parvovirus and *Borrelia burgdorferi* antigen OspA.

| Component | Abbreviation |
|---|---|
| Canine Distemper Virus, Rockborn ($CDV_R$) or Onderstepoort ($CDV_o$) | D |
| Canine Adenovirus Type 2 ($CAV_2$) | A |
| Canine Coronavirus, MLV ($CCV_L$) | C |
| Canine parainfluenza Type 2 (CPi) | Pi |
| Canine Parvovirus, ($CPV_{XL}$) | $P_{XL}$ |

These components were prepared from modified live virus (available from Rhone Merieux, Inc., Athens, Ga., U.S.A.). The vaccines had the following formulation of components.

| Component | Titer/ml ($Log_{10}$) |
|---|---|
| D | 5.2 or 5.4 ($CDV_R$ = 5.2, $CDV_o$ = 5.4) |
| A | 7.4 |
| C | 6.6 |
| Pi | 7.5 |
| $P_{XL}$ | 5.3 |

The vaccine was prepared as two separate components:

The first component was the Canine Distemper-Adenovirus Type 2-Coronavirus-Parainfluenza-Parvovirus$_{XL}$, Modified Live Virus, designated DACPiP$_{XL}$, which was lyophilized in one vial and did not contain any adjuvant. The second component was *Borrelia burgdorferi*. B31 Outer Surface Membrane Protein A (OspA) was produced through recombinant technology as set forth in Example 1 (designated Ly) or OspA.

The second component was the liquid component used to rehydrate the lyophilized components of the vaccine prior to inoculation. The OspA fraction did not contain any adjuvant.

The lyophilized vaccine DACPIP$_{XL}$ was tested as satisfactory for virus identity and titer, sterility, Mycoplasma, and safety. The lyophilized cake was rehydrated with Ly, containing 13 μg/ml OspA. The OspA vaccine was tested for sterility.

The lack of interference of the OspA diluent upon the lyophilized components of the vaccine was determined by in vitro viricidal testing conducted according to the guidelines of the Code of Federal Regulations, 9 C.F.R. 113.35.

The lack of interference of the lyophilized viral fraction upon the OspA diluent was determined by comparing the serologic titers of dogs vaccinated with the combination vaccine (DACPiP$_{XL}$+OspA) to titers from dogs vaccinated with OspA alone (see Example 2).

As DACPiP$_{XL}$+OspA was the result of combining two separate vaccines that have already undergone extensive efficacy testing, only a small number of dogs were challenged to show that the lyophilized viral component of the vaccine does not interfere with the protection elicited against Lyme Disease by the OspA fraction, and vice versa.

Twenty dogs were randomized according to age, breed, and sex, and were housed together. Ten dogs were vaccinated with the DACPi$_{XL}$+OspA combination vaccine, five dogs were vaccinated with OspA alone (as per Example 2), and five dogs served as untreated controls.

Dogs received two doses of vaccine (1 ml/dog), administered subcutaneously (SC) at a three week interval, according to the following schedule:

| NUMBER | VACCINE | ROUTE | BLEED DATE | CHALLENGE |
|---|---|---|---|---|
| 10 | DACPiP$_{XL}$ + LY | SQ | DAY 0, 21, 35 | DAY 35 |
| 5 | LY | SQ | DAY 0, 21, 35 | DAY 35 |
| 5 | DACPiP$_{XL}$ | SQ | DAY 0, 21, 35 | DAY 35 |
|  | CONTROLS |  |  |  |

Dogs were bled before each vaccination (days 0 and 21), before challenge (day 35), and before each biopsy. Specific antibody to OspA was detected by an ELISA test. Anti-OspA was detected in dogs receiving OspA or DACPiP$_{XL}$+OspA.

All dogs were observed immediately following vaccination for adverse reactions, including anaphylaxis. Additionally, dogs were monitored daily by animal technicians for local and systemic adverse vaccine reactions, including fever, anorexia, vomiting, or lethargy. Prior to the second injection, the previous vaccination site was palpated for any abnormal reaction, including granuloma formation. No adverse reactions were observed.

All dogs were challenged two weeks after the second vaccination with ticks infected naturally with *Borrelia burgdorferi* (see Example 2).

Skin punch biopsies were obtained from dogs at one, two, and three months post-challenge. Biopsy material was cultured for spirochete reisolation according to the protocol outlined in Example 2.

A lack of interference of the lyophilized viral fraction of the combination vaccine, upon the OspA diluent, was assessed by comparing the spirochete reisolation rate in vaccinated dogs as compared to that in untreated controls.

To show that the OspA fraction does not adversely affect the lyophilized viral components in the combination Lyme vaccine, viricidal testing was performed. All viral components were titrated after hydration with Ly, and that titration was compared to one in which viral components are rehydrated with sterile water.

Interpretation of in Vivo and in Vitro Results

Efficacy of the combination vaccine was determined in vivo by serology titers and by results of spirochete reisolation, and in vitro by viricidal testing. OspA antibody levels and results of spirochete reisolation, in dogs vaccinated with the combination vaccine (DACPIP$_{XL}$+Ly), were compared to those observed in dogs vaccinated with Ly alone, and to levels in untreated controls.

The combination vaccine is considered efficacious because:

(1) Antibody levels in combo vaccinates were similar to levels in dogs receiving the monovalent Ly vaccine. Antibody levels in vaccinates were also be significantly higher than levels in untreated controls;

(2) 100% of the vaccinated dogs were negative for spirochete reisolation, while 80% (4/5) of the untreated controls were positive for spirochetes; and (3) There is no loss in virus titer when the lyophilizied viral cake is rehydrated with the Ly diluent as compared to sterile water.

The results are shown in Table 9.

TABLE 9

Canine Combination Efficacy Study
Anti-OspA ELISA Levels

| Animal # | Vaccine | Week 0 (Vax 1) | Week 2 (Vax 2) | Week 4 | Week 8 |
|---|---|---|---|---|---|
| 700 | Osp A | <25 | 50 | 800 | 400 |
| 711 | 13 µg/ml | <25 | 3200 | 6400 | 1600 |
| 4D587 | lot #041795 | <25 | 25 | 200 | 25 |
| 283 | and | <25 | 200 | 12,800 | 400 |
| 4D547 | DACPiP$_{XL}$ | <25 | <25 | <25 | 100 |
| 904 | lot #43001 | <25 | 50 | 3200 | 100 |
| 4D517 |  | <25 | 400 | 3200 | 400 |
| 961 |  | <25 | <25 | 1600 | 100 |
| 4D581 |  | <25 | 3200 | 12,800 | 1600 |
| 982 |  | <25 | 50 | 12,800 | 800 |
| 4E455 | Osp A | <25 | 25 | 800 | 25 |
| 4E403 | 13 µg/ml | <25 | 800 | 6400 | 1600 |
| 381 | lot #041795 | <25 | 800 | 6400 | 800 |
| 688 | alone | <25 | 400 | 800 | 100 |
| 4D515 |  | <25 | 50 | 6400 | 800 |
| 449 | DACPiP$_{XL}$ | <25 | <25 | <25 | <25 |
| 844 | lot #43001 | <25 | <25 | <25 | <25 |
| 4E457 | alone | <25 | <25 | <25 | <25 |
| 4D497 | (controls) | <25 | <25 | <25 | <25 |
| 4E439 |  | <25 | <25 | <25 | <25 |

*All dogs received two subcutaneous vaccinations, at a three week interval.
Ly = Lyme OspA; DACPiP$_{XL}$ = canine distemper, adenovirus, corona, parainfluenza, and parvovirus, modified live vaccine.
Values >50 = significant OspA antibody levels.

Example 4

Efficacy of OspA Vaccines in Horses

Ten horses were used for this study. Their numbers are 74, 75, 76, 77, 93, 95, 96, 97, 98 and 99.

The monovalent vaccines (designated Ly; 100 µg/dose OspA; and 30 µg/dose, were made from recombinant technology as set forth in Example 1 (B31). The combination vaccine (designated rabies/Ly) consists of Imrab (available from Rhone Merieus, Inc., Athens, Ga.) plus 30 µg/ml of B31 OspA as prepared in Example 1 (B31).

All horses were vaccinated intramuscularly (IM) with two doses ov vaccine, given at a two week interval, according to the following protocol:

| Group | No. | Vaccine |
|---|---|---|
| 1 | 4 | Rabies/Ly combo (30 µg/ml) |
| 2 | 4 | 100 µg/ml Ly |
| 3 | 2 | 30 µg/ml Ly |

Horses were bled before each vaccination and at one, two and three weeks after the second vaccination. Serological results were determined by ELISA (as modified by the use of horse antiserum). Rabies antibody titers were determined, in horses vaccinated with the combo, as the results of OspA serology was encouraging.

All horses were observed for 30 minutes to one hour following each vaccination for signs characteristic of anaphylaxis. Following the initial observation period, vaccination sites were checked prior to the administration of the second vaccination for the appearance of local injection reactions (lumps, etc.). Additionally, each horse was observed daily for the appearance of adverse vaccine reactions (fever, depression, anorexia, etc). All daily observations continued until one week after the final vaccination. No adverse reactions were observed.

Efficacy of the vaccines was assessed by evaluating the levels of anti-OspA antibodies in vaccinated horses and comparing those levels to pre-bleed levels.

The results are shown in Table 10. The results indicate that horses can be protected against Lyme Disease by either the monovalent or multivalent OspA vaccine; and, that as to the multivalent vaccine, no efficacy interference is observed.

TABLE 10

Equine Lyme Vaccination Trial
Anti-OspA ELISA Levels

| Animal # | Vaccine | Week 0 | Week 1 | Month 4 | Month 5 | Month 6 |
|---|---|---|---|---|---|---|
| 96 | OspA | 25 | n.b. | 200 | 800 | 200 |
| 99 | 30 µg/ml | <25 | n.b. | <25 | 800 | 100 |
| 76 | OspA | n.b. | n.b. | 800 | 3200 | 1600 |
| 74 | 100 |  n.b. |  | 400 | 12.8k | 6400 |
| 95 | µg/ml | 25 | n.b. | 50 | 1600 | 400 |
| 75 |  | n.b. | 100 | 400 | 3200 | 800 |
| 93 | OspA | <25 | n.b. | 400 | 25.6k | 6400 |
| 98 | 30 | n.b. | 200 | 800 | 6400 | 1600 |
| 97 | µg/ml + | <25 | n.b. | 400 | 6400 | 1600 |
| 77 | Imrab lot #12160 | 25 | n.b. | 800 | 6400 | 1600 |

*All horses received two intramuscular injections, at a three week interval.
Imrab = commercial adjuvanted inactivated rabies vaccine.
*n.b. = not bled; values >50 indicate significant OspA antibody levels.

Example 5

Canine Lyme: Safety, Efficacy and Lack of Interference of a Lyme Combination Vaccine This Example further evaluates the safety, efficacy and interference of a Lyme combination vaccine (recDACPiP$_{XL}$+OspA).

Thirty-four (34) beagles were randomly divided into two groups (22 vaccinates and 12 controls). Vaccinates received two doses of a combination vaccine (recDACPiP$_{XL}$+OspA) subcutaneously, while controls were vaccinated with viral components alone (recDACPiP$_{XL}$). All dogs were challenged 7 weeks after the second vaccination with naturally infected ticks. Dogs were tested for OspA antibodies at regular intervals by ELISA serology. To confirm efficacy of the vaccine against *Borrelia burgdorferi* challenge, dogs were biopsied and skin samples cultured for spirochete reisolation. Additionally, lack of interference testing and viricidal assays were performed to confirm that the OspA diluent has no deleterious effect upon viral vaccine components.

Safety: No adverse local or generalized reactions were found at any time following injection.

Efficacy Summary:

TABLE 11

| Group | # Dogs | Lyme Postavaccinal Seroconversion | | Postchallenge Spirochete Reisolation | |
|---|---|---|---|---|---|
| | | 1st Injection | 2nd Injection | 1st Biospy | 2nd Biopsy |
| recDACPiP$_{XL}$ + OspA | 22 | 12/21* = 57.1% | 22/22 = 100% | 1/22 = 4.8% | 0/22 = 0% |
| recDACPiP$_{XL}$ alone | 12 | 0/11* = 0% | 0/12 = 0% | 4/12 = 33.4% | 9/12 = 75% |

*One dog was not bled.

Lack of interference: Both viricidal assays and lack of interference testing showed that the OspA diluent does not have a deleterious effect upon the viral components in the combination vaccine.

Thus, the Lyme Combination Vaccine (recDACPiP X +OspA):

is safe in 8 to 10 weeks old puppies;

is very antigenic and induces OspA seroconversion in 100% of vaccinated dogs;

protects vaccinates against spirochete infection and dissemination after a natural tick challenge; and does not interfere with lyophilized viral vaccine components as demonstrated by in vivo lack of interference testing or in vitro viricidal assays.

Abbreviations Used

| Vaccine Component | Abbreviation |
|---|---|
| Outer Surface protein A from *Borrelia burgdorferi* (OspA) (see previous Examples) | OspA |
| Canine Distemper Virus; Canarypox Vector (recCDV) | D |
| Canine Adenovirus Type 2 (CAV2) | A |
| Canine Parainfluenza Virus (CPi) | Pi |
| Canine Parvovirus (P$_{XL}$) | P$_{XL}$ |
| Canine Coronavirus (CCV) | C |

A combination vaccine, which could immunize dogs against Lyme disease and simultaneously provide protection against other canine pathogens, would offer veterinarians an important alternative for infectious disease prophylaxis.

The present study was conducted to determine the safety, efficacy, and lack of interference of the inventive combination vaccine. The combination vaccine was composed of an OspA diluent (designated OspA) and a lyophilized viral cake containing recombinant Canine Distemper virus-Adenovirus Type 2-Coronavirus-Parainfluenza-Parvovirus (designated (recDACPiP$_{XL}$)).

Materials and Methods

Animals

Thirty-four Beagle puppies (both sexes; eight weeks of age; negative for Lyme (*Borrelia burgdorferi*) and Leptospira antibodies) were obtained from Ridglan Farms (Mount Horeb, Wis.). The puppies were divided randomly into two groups and vaccinated as follows:

| GROUP | DOG # | VACCINE | ROUTE | CHALLENGE |
|---|---|---|---|---|
| 1 | 22 | recDACPiP$_{XL}$ + OspA | SC | 7 weeks |
| 2 | 12 | recDACPiP$_{XL}$ + sterile diluent | SC | 7 weeks |

Vaccine Preparation: The OspA vaccine was obtained as in Example 1. The lyophilized viral component was obtained as a prelicense serial. Titrations of the lyophilized cake are as follows:

| VACCINE | recCDV | CAV2 | CCV | CPI | P$_{XL}$ |
|---|---|---|---|---|---|
| reDACPiP$_{XL}$ | 7.3 | 5.6 | 4.5 | 6.5 | 5.2 |

Vaccine Protocol: Dogs received two doses of each vaccine (1 ml/dog) subcutaneously at a three week interval. Signs of anaphylaxis, including difficulty in breathing, itching, and edema, were monitored for the initial 15 minutes following injection. Additionally, the animal caretakers observed the dogs continuously for the first hour after vaccination, and then at daily intervals for fourteen days after each injection. Signs monitored included swelling, pain, tenderness, and scratching at the injection site. Prior to administration of the second injection, the site of the primary vaccination was palpated for swelling and tenderness.

Serology

Blood was taken for serology before each vaccination and at monthly intervals thereafter. OspA titers were determined by ELISA.

Lack of Interference Testing: To demonstrate a lack of interference of the OpsA diluent upon viral components in the combination vaccine, serum neutralization titers were determined and the GMT for Group I (vaccinated with recDACPiP$_{XL}$+OspA) compared to titers in Group II (vaccinated with recDACPiP$_{XL}$ alone).

In Vitro Viricidal Testing: To demonstrate that the ospA diluent does not interfere with the titers of the viral components in the combination vaccine, in vitio viricidal testing was conducted according to 9 CFR guidelines (113.35).

Tick Challenge: To verify that viral components did not interfere with the protection elicited with the OspA fraction of the combination vaccine, all dogs were challenged with *B. burgdorferi* seven weeks after vaccination. This challenge used naturally infected ticks gathered in an area endemic for Lyme Disease. The rate of *Borrelia burgdorferi* infection of these ticks was determined to be 60%.

Skin Biopsy and Spirochete Reisolation

All dogs were biopsied at one and two months postchallenge. The skin around the site of tick attachment was shaved, prepped with Betadine surgical scrub, anesthetized with 2% lidocaine injected intradermally, and punch-biopsied using a Baker Skin Punch. Skin samples were placed in tubes containing culture medium (BSK media with heat-inactivated rabbit serum and antibiotics) and transported to the laboratory. Tubes were supplemented with additional media and placed in a candle jar. The jar was incubated for six weeks. Tubes were examined weekly for the presence of spirochetes, using a dark field microscope. At least ten fields were examined with a 40X objective before the sample was considered negative.

Vaccine Safety: All vaccinated dogs were monitored for adverse reactions (including anaphylaxis) for the first fifteen minutes following vaccination by the PI, and for the next fourteen days following each vaccination by the animal caretakers. No adverse systemic reactions were observed at any time following vaccination with the Lyme combination vaccine. Additionally, no swelling, pain, tenderness, or itching was demonstrated at the injection site during the two week period following vaccination.

OspA Antibody Titers (See Table 12): Antibody to OspA was determined by ELISA. Blood was drawn on day 0 (prebleed; prior to the administration of the first vaccination); day 14 (prior to receiving a second vaccination); day 42 (prior to challenge); and at monthly intervals thereafter.

Table 12 lists the ELISA values. Following the first vaccination, twelve of the twenty-one vaccinates bled (57.1%) had seroconverted, as determined by an increase in OspA antibody levels of at least four fold. Two weeks after the second vaccination, all twenty-two dogs (100%) vaccinated with recDACPiP$_{XL}$ alone had seroconverted to OspA. The majority of vaccinates still exhibited significant OspA antibody titers before challenge (19/22=86.4%). None of the controls, vaccinated with recDACPiP$_{XL}$ alone, showed a serological response to the OspA antigen.

In both groups, antibody levels rose very little after tick challenge. OspA antibody is not expressed in humans with Lyme Disease until late in the course of infection and it appears that the same is true in canines with natural infection.

Lack of Interference Testing (See Table 13): Sera was obtained from dogs at day 0 (prior to first vaccination) and day 35 postvaccination. Serum neutralization titers of the viral antigens in the combination vaccine were determined for each dog at both dates. Geometric mean titers (GMT) and the standard deviation (SD) was calculated for the group vaccinated with recDACPiP$_{XL}$ alone and compared to the GMT for the group receiving the Lyme combination vaccine (recDACPiP$_{XL}$+OspA).

The puppies used in these study were negative for Lyme or Leptospira vaccination or exposure, but were not raised in Specific-Pathogen-Free conditions. Therefore, prebleed results on day 0 showed titers to the viral components in the lyophilized fractions of the vaccine. Following vaccination, titers of all components were elevated as expected.

Comparison of the individual titers (analyzed using the student's t test, with p<0.05 considered as significant) showed no difference in serum neutralizing titers in dogs vaccinated with recDACPiP$_{XL}$+OspA as compared to titers of those receiving recDACPiP$_{XL}$ alone. Therefore, there is no significant interference from the OspA diluent upon any of the viral components of the vaccine.

In Vitro Viricidal Testing (See Table 14): In vitro viricidal testing compared titers for each component of the viral vaccine rehydrated with OspA diluent to titers determined when the vaccine was rehydrated by sterile water. Comparison of these titers showed that the variation was within acceptable limits for each of the viral components in the Lyme combination vaccine (less than 0.5 log difference in titer).

Spirochete Reisolation (See Table 15): Skin biopsies were performed for all dogs at one and two months postchallenge. Biopsies were cultured for six weeks and examined for spirochete reisolation. Results show that only one dog vaccinated with the combination Lyme vaccine (XBY) was positive for spirochetes (4.5%), and that dog was only positive at the first biopsy date. None of the twenty-two dogs vaccinated with recDACPiP$_{XL}$+OspA was positive for spirochetes at the second biopsy (0%).

Spirochetes were reisolated from biopsy samples taken from three of the twelve control dogs at one month postchallenge (25%), while nine of the controls were positive by the second biopsy (75%).

Lyme Disease (LD), caused by the pathogenic spirochete *Borrelia burgdorferi,* is currently the most common tickborne disease in humans. Additionally, canine LD is being reported more frequently as awareness of infection in dogs increases among veterinarians.

It is known that one of the major outer surface proteins of *Borrelia burgdorferi,* designated OspA, is a potent immunogen and provides protection against spirochete infection in a variety of animals. The purified OspA protein, produced in ample amounts by recombinant technology, is also the basis of two human vaccines currently undergoing clinical trials.

A combination vaccine, which could immunize dogs against Lyme disease and simultaneously provide protection against other canine pathogens, would offer veterinarians an important alternative for infectious disease prophylaxis.

The purpose of this Example was to determine the efficacy, safety and lack of interference of such a combination vaccine. The vaccine contained a lyophilized viral cake containing recombinant Canine Distemper virus-Adenovirus Type 2-Coronavirus-Parainfluenza-Parvovirus (designated (recDACPiP$_{XL}$)) and was rehydrated with an OspA diluent. Twenty-two puppies were vaccinated with the combination vaccine (recDACPiP$_{XL}$+OspA), while twelve controls were vaccinated with the lyophilized viral cake rehydrated with sterile water (recDACPiP$_{XL}$). All puppies received two subcutaneous vaccinations, three weeks apart, and then were challenged with *Borrelia burgdorferi* infected ticks.

The natural tick challenge model was used in this Example. Following challenge all dogs were biopsied at one and two months post-challenged and samples cultured for spirochete reisolation. Results showed that only one of the puppies vaccinated with the Lyme combination vaccine was transiently positive for spirochete reisolation, because this dog, and all other puppies vaccinated with the combination vaccine, was negative for spirochete dissemination at the second biopsy. In contrast, spirochetes were reisolated from 75% of the dogs vaccinated with recDACPiP$_{XL}$ alone at the second biopsy date.

OspA antibody results have been determined for all of the dogs. All of the puppies vaccinated with the combination vaccine (recDACPiP$_{XL}$+OspA) seroconverted after receiving two injections, although none of the controls showed an increase in OspA antibody levels following vaccination with the lyophilized viral components alone.

OspA titers in control animals, shown to be infected by biopsy, did not rise significantly following tick challenge. In humans it is known that OspA antibodies are not present in early Lyme Disease; the results from this study indicate that such may also be the case for canine infection.

The safety of the OspA combination vaccine was also demonstrated by this study. No adverse systemic or local reactions were noted at the time of vaccination, or in the two week period following each injection.

The Lyme Combination Vaccine of the Invention (recDACPiP$_{XL}$+OspA)
  is safe in 8 to 10 weeks old puppies;
  is very antigenic and induces OspA seroconversion in 100% of vaccinated dogs;
  protects vaccinates against spirochete infection and dissemination after a natural tick challenge, as demonstrated by spirochete reisolation; and
  does not interfere with lyophilized viral vaccine components as demonstrated by in vivo lack of interference testing and in vivo viricidal assays.

TABLE 12

Results of Antibody Titers to OspA

| Vaccine | Animal # | Prebleed day 0 | $V_2$ day 14 | day 28 | Pre-challenge day 42 | Biopsy$_1$ day 92 | Biopsy$_3$ day 126 | day 155 | day 232 |
|---|---|---|---|---|---|---|---|---|---|
| rDACPiP$_{XL}$ + OspA | WIX | <25 | 50 | 12.8k | 800 | 200 | 50 | 25 | <25 |
| | XBY | <25 | NB | 1600 | 200 | 100 | <25 | <25 | <25 |
| | XDY | NB | <25 | 200 | 100 | 100 | 50 | NB | NB |
| | XCY | <25 | 25 | 1600 | 400 | 25 | <25 | <25 | <25 |
| | XAY | <25 | 200 | 6400 | 800 | 200 | NB | 50 | 100 |
| | XGY | <25 | 50 | 6400 | 50 | 50 | <25 | <25 | <25 |
| | XHY | <25 | 100 | 3200 | 400 | 100 | <25 | <25 | <25 |
| | XIY | <25 | 50 | 3200 | 400 | 50 | <25 | <25 | <25 |
| | XJY | <25 | 200 | 6400 | 400 | 100 | <25 | <25 | <25 |
| | XKY | <25 | 50 | 800 | NB | <25 | <25 | <25 | <25 |
| | WXW | <25 | <25 | 1600 | 400 | 50 | <25 | 25 | <25 |
| | WYW | <25 | 25 | 3200 | 800 | 200 | 25 | 100 | 100 |
| | WTX | <25 | <25 | 3200 | 800 | 400 | 100 | 50 | 100 |
| | WUX | <25 | 50 | 3200 | 200 | 50 | 100 | 25 | 25 |
| | WVX | <25 | 50 | 800 | 100 | 40 | <25 | 25 | 25 |
| | WWX | <25 | 400 | 12.8K | 1600 | 400 | 100 | 50 | 50 |
| | WSX | <25 | 50 | 25.6K | 1600 | 800 | 200 | 200 | 200 |
| | WLX | <25 | <25 | 800 | 100 | NB | <25 | <25 | <25 |
| | WOW | NB | <25 | 400 | 100 | <25 | <25 | <25 | <25 |
| | WPW | 25 | <25 | 400 | 50 | 50 | <25 | <25 | <25 |
| | WQW | NB | <25 | 800 | 100 | 100 | <25 | <25 | 50 |
| | WRW | <25 | 50 | 3200 | 100 | <25 | <25 | <25 | 50 |
| rDACPiP$_{XL}$ ALONE | VVX | <25 | <25 | 50 | <25 | 50 | <25 | <25 | <25 |
| | VXW | <25 | <25 | <25 | 50 | 100 | <25 | <25 | <25 |
| | VYW | <25 | <25 | <25 | 25 | 100 | <25 | <25 | 25 |
| | WBX | <25 | <25 | <25 | <25 | 50 | <25 | <25 | <25 |
| | WCX | <25 | <25 | <25 | <25 | <25 | <25 | <25 | <25 |
| | WDX | <25 | <25 | <25 | <25 | 50 | <25 | <25 | <25 |
| | WAX | <25 | <25 | 25 | <25 | <25 | <25 | <25 | <25 |
| | WEX | <25 | <25 | 25 | <25 | 25 | <25 | <25 | <25 |
| | WZZ | <25 | <25 | 25 | <25 | 25 | <25 | 25 | <25 |
| | WGX | NB | <25 | <25 | <25 | <25 | <25 | <25 | <25 |
| | WFX | <25 | NB | 50 | 25 | 25 | <25 | 25 | 25 |
| | WHX | <25 | <25 | <25 | 50 | 50 | 25 | 50 | 100 |

TABLE 13

Serum Antibody Levels: Lack of Interference of the Lyme Diluent upon Viral Components of a Combination Vaccine

| ANTIGEN | VACCINE | DAY 0[1] GMT | DAY 0[1] SD | DAY 35 GMT | DAY 35 SD |
|---|---|---|---|---|---|
| recCDV | recDACPiP$_{XL}$ + OspA | 1.05 | 0.37 | 1.78 | 0.46 |
| | recDACPiP$_{XL}$* | 1.01 | 0.35 | 1.66 | 0.65 |
| CAV | recDACPiP$_{XL}$ + OspA | 2.24 | 0.25 | 2.48 | 0.27 |
| | recDACPIp$_{XL}$ | 2.17 | 0.19 | 2.33 | 0.29 |
| CPI | recDACPiP$_{XL}$ | 1.52 | 0.33 | 2.12 | 0.18 |
| | recDACPiP$_{XL}$ | 1.62 | 0.31 | 2.10 | 0.16 |
| P$_{XL}$ | recDACPiP$_{XL}$ + OspA | 2.00 | 0.00 | 3.72 | 0.78 |
| | recDACPiP$_{XL}$ | 2.00 | 0.00 | 3.68 | 0.62 |
| CCV | recDACPiP$_{XL}$ + OspA | 1.51 | 0.29 | 2.53 | 0.40 |
| | recDACPiP$_{XL}$ | 1.31 | 0.49 | 2.78 | 0.42 |

[1]Date of first vaccination
*Rehydrated with sterile diluent
GMT: Geometric Mean Titer
SD: Standard Deviation

TABLE 14

Titers of Lyophilized Viral Components With and Without Lyme Diluent (Viricidal Effect)

| VACCINE | TITERS OF VIRAL FRACTIONS[1] | | | | |
|---|---|---|---|---|---|
| | recCDV | CAV2 | CCV | CPi | P$_{XL}$ |
| recDACPiP$_{XL}$[2] | 7.6 | 6.2 | 4.6 | 6.0 | 5.3 |
| recDACPiP$_{XL}$ + OspA | 7.7 | 5.7 | 4.4 | 5.8 | 5.1 |

[1]Average of two replicates
[2]Lyophilized vaccine rehydrated with sterile diluent

TABLE 15

Results of OspA Seroconversion and Spirochete Reisolation following Challenge

| VACCINE | SEROCONVERSION | | SPIROCHETE REISOLATION | |
|---|---|---|---|---|
| | 1ST INJECTION | 2ND INJECTION | 1ST BIOPSY | 2ND BIOPSY |
| recDACPiP$_{XL}$ | 12/21* = 57.1% | 22/22 = 100% | 1/22 = 4.5% | 0/22 = 0.0% |
| recDACPiP$_{XL}$ + OspA | 0/11* = 0.0% | 0/12 = 0.0% | 3/12 = 25% | 9/12 = 75% |

*One dog not bled

Having thus described in detail preferred embodiments of the present invention, it is to be understood that the invention defined by the appended claims is not to be limited by particular details set forth in the above description as many apparent variations thereof are possible without departing from the spirit or scope thereof.

REFERENCES

1. Barbour, A. G. and Fish, D. The biological and social phenomenon of Lyme Disease. *Science.* 1993, 260, 1610–1616.
2. Fikrig, E., Barthold, S. W., Kantor, F. S. and Flavell, R. A. Protection of mice against the Lyme disease agent by immunizing with recombinant OspA. *Science.* 1990, 250, 553–556.
3. Erdile, L. f., Brandt, M., Warakomski, D. J., Westrack, G. J., Sadziene, A., Barbour, A. G. and Mays, J. P. Role of attached lipid in immunogenicity of *Borrelia burgdorferi* OspA. *Infect. Immun.* 1993, 61, 81–90. See also U.S. Ser. No. 08/373,455.
4. Keller, D., Kister, F. T., Marks, D. H., Hosback, P., Erdile, L. F. and Mays, J. P. Safety and immunogenicity of a recombinant outer surface protein A Lyme vaccine. *J. Am. Med. Assoc.* 1994, 271, 1764.

What is claimed is:

1. An immunological composition consisting essentially of: (i) an isolated, purified *Borrelia burgdorferi* antigen consisting essentially of OspA, or a vector expressing the antigen; (ii) at least one additional antigen of a mammalian pathogen other than *Borrelia burgdorferi*, or a vector expressing the at least one additional antigen; and optionally (iii) a pharmaceutically or veterinarily acceptable carrier; wherein the at least one additional antigen is a rabies virus antigen; or the at least one additional antigen consists essentially of a combination of a canine distemper antigen, and adenovirus antigen, a coronavirus antigen, a parinfulenza antigen, and a parvovirus antigen; or the at least one additional antigen consists essentially of a combination of a rabies antigen, a canina distemper antigen, an adenovirus antigen, a coronavirus antigen, a parainfluenza antigen, and a paravovirus antigen.

2. An immunological composition consisting essentially of: (i) an isolated, purified *Borrelia burgdorferi* antigen consisting essentially of OspA antigen, or a vector expressing the OspA antigen; and (ii) at least one additional antigen of a mammalian pathogen other than *Borrelia burgdorferi*, or a vector expressing the at least one additional antigen; and optionally (iii) a pharmaceutically or veterinarily acceptable carrier; wherein the at least one additional antigen consists essentially of an antigen selected from the group consisting of: a rabies virus antigen, a canine distemper antigen, and adenorivus antigen, a coronavirus antigen, a parainfluenza antigen, a paravovirus antigen, and mixtures thereof.

3. An immunological composition comprising: (i) an isolated, purified *Borrelia burgdorferi* antigen consisting essentially of OspA, or a vector expressing the antigen; and (ii) at least one additional antigen of a mammalian pathogen other than *Borrelia burgdorferi*, or a vector expressing the at least one additional antigen; and optionally (iii) a pharmaceutically or veterinarily acceptable carrier; wherein the at least one additional antigen is a rabies virus antigen; or the, at least one additional antigen comprises a combinational of a canine distemper antigen, an adenovirus, antigen, a coronavirus antigen, a parainfluenza antigen and a parvovirus antigen; or the at least one additional antigen comprises a combination of a rabies antigen, a canine distemper antigen, an adenovirus antigen, a coronavirus antigen, a parainfluenza antigen, and a parvovirus antigen; and the at least one additional antigen is not a Leptospira antigen that interferes with OspA.

4. An immunological composition comprising: (i) an isolated, purified *Borrelia burgdorferi* antigen consisting essentially of OspA antigen, or a vector expressing the OspA antigen; and (ii) at least one additional antigen of a mammalian pathogen other than *Borrelia burgdorferi*, or a vector expressing the at least one additional antigen; and optionally (iii) a pharmaceutically or veterinarily acceptable carrier; wherein the at least one additional antigen is selected from the group consisting of: a rabies virus antigen, a canine distemper antigen, an adenovirus anitigen, a coronavirus antigen, a parainfluenza antigen, a parvirus antigen, and mixtures thereof; and the at least one additional antigen is not a Leptospira antigen the interferes with OspA.

5. An immunological composition consisting essentially of: (i) an isolated, purified *Borrelia burgdorferi* antigen consisting essentially of OspA antigen, or a vector expressing the OspA antigen; and (ii) at least one modified live virus selected from the group consisting of canine distemper virus, canine adenovirus, canine coronavirus, canine parainfluenza virus, canine parvovirus, and mixtures thereof; and optionally (iii) a pharmaceutically or veterinarily acceptable carrier.

6. The immunological composition of any one of claims 1 or 3 wherein (i) is the isolated, purified *Borrelia burgdorferi* OspA antigen.

7. The immunological composition of claim 6 wherein the isolated, purified OspA is an isolated, purified, lipidated OspA.

8. The immunological composition of claim 7 which is without any immunogenicity enhancing adjuvant.

9. The immunological composition of any one of claims 1 or 3 wherein (i) is the vector expressing isolated, purified *Borrelia burgdorferi* OspA antigen.

10. The immunological composition of claim 1 wherein (ii) consists essentially of the vector that expresses the at least one additional antigen.

11. The immunological composition of claim 1 wherein (ii) is the at least one additional antigen from a pathogen other than *Borrelia burgdorferi*.

12. The immunological composition of any one of claims 1 or 3 wherein the at least one additional antigen is a rabies virus antigen.

13. The immunological composition of claim 1 wherein the at least one additional antigen consists essentially of the combination of a canine distemper antigen, an adenovirus antigen, a coronavinis antigen, a parainfluenza antigen, and a parvovirus antigen.

14. A method for eliciting an immunological response in a mammal susceptible to Lyme Disease and the at least one additional mammalian pathogen other than *Borrelia burgdorferi* comprising administering to the mammal a composition as claimed in any one of claims 1 or 3.

15. A method for eliciting an immunological response in a dog or pup comprising administering to the dog or pup a composition as claimed in any one of claims 1, 2, 3, 4, or 5.

16. A method for eliciting an immunological response in a horse comprising administering to the horse a composition as claimed in any one of claims 1, 2, 3 or 4.

17. The composition of any one of claims 2 or 4 wherein (i) consists essentially of the isolated, purified OspA antigen, and (ii) is the at least one additional antigen from a pathogen other than *Borrelia burgdorferi*.

18. the immunological composition of claim 1 wherein the at least one additional antigen consists essentially of the combination of a rabies antigen, a canine distemper antigen, an adenovirus antigen, a coronavirus antigen, a parainfluenza antigen, and a parvovirus antigen.

19. The immunological composition of claim 3 wherein the at least one additional antigen comprises the combination of a rabies antigen, a canine distemper antigen, an adenovirus antigen, a coronavirus antigen, a parainfluenza antigen, and a parvovirus antigen.

20. The immunological composition of claim 3 wherein the at least one additional antigen comprises the combination of a canine distemper antigen, an adenovirus antigen, a coronvirus antigen, at parainfluenza antigen, and a parvovirus antigen.

21. The immunological composition of claim 3 wherein (ii) consist essentially of the vector that expresses the at least one additional antigen.

22. A method for eliciting an immunological response in a cat comprising administering to the cat a composition as claimed in any one of claims 1, 2, 3 or 4.

23. An immunological composition as claimed in any one of claims 1, 2, 3 or 4, which additionally contains an immunogenicity-enhancing adjuvant.

* * * * *

UNITED STATES PATENT AND TRADEMARK OFFICE
CERTIFICATE OF CORRECTION

PATENT NO. : 6,368,603 B1
DATED : April 9, 2002
INVENTOR(S) : Judy Jarecki-Black It is certified that error appears in the above-identified patent and that said Letters Patent is hereby corrected as shown below:

<u>Column 39,</u>
Lines 63-64, change "and adenorivus" to -- an adenovirus --.

<u>Column 40,</u>
Line 20, change "adenovirus, antigen" to -- adenovirus antigen --.
Line 37, change "parvirus" to -- parovirus --.

<u>Column 41,</u>
Line 21, change "the" to -- The --.

Signed and Sealed this

Eleventh Day of June, 2002

Attest:

JAMES E. ROGAN
*Attesting Officer*     *Director of the United States Patent and Trademark Office*